United States Patent
Aceves et al.

(10) Patent No.: US 12,268,777 B2
(45) Date of Patent: Apr. 8, 2025

(54) COMPOSITIONS AND METHODS FOR TREATING EOSINOPHILIC DISORDERS

(71) Applicant: The Regents of the University of California, Oakland, CA (US)

(72) Inventors: Seema S. Aceves, Solana Beach, CA (US); Ranjan Dohil, San Diego, CA (US); Quan Nhu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 176 days.

(21) Appl. No.: 18/150,152

(22) Filed: Jan. 4, 2023

(65) Prior Publication Data

US 2023/0218518 A1     Jul. 13, 2023

Related U.S. Application Data

(62) Division of application No. 16/894,784, filed on Jun. 6, 2020, now Pat. No. 11,547,664.

(60) Provisional application No. 62/858,951, filed on Jun. 7, 2019.

(51) Int. Cl.
| | |
|---|---|
| *A61K 9/00* | (2006.01) |
| *A61K 9/20* | (2006.01) |
| *A61K 9/48* | (2006.01) |
| *A61K 31/426* | (2006.01) |
| *A61K 31/573* | (2006.01) |
| *A61K 47/32* | (2006.01) |
| *A61K 47/38* | (2006.01) |

(52) U.S. Cl.
CPC ............. *A61K 9/0095* (2013.01); *A61K 9/20* (2013.01); *A61K 9/4808* (2013.01); *A61K 31/426* (2013.01); *A61K 31/573* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 2002/0198203 A1 | 12/2002 | Vitou et al. | |
| 2009/0111777 A1 | 4/2009 | Ueshima et al. | |
| 2011/0053986 A1* | 3/2011 | Finch | A61K 31/58 514/342 |

OTHER PUBLICATIONS

Fischl et al. (Thiazolidinediones (TZDs or Glitazones) for Type 2 Diabetes; Jul. 14, 2014. (Year: 2014).*
Basicmedical Key (19 Visosity-Inducing Agents, Jun. 1, 2016).
Fishcl et al., Thiazolidinediones (TZDs or Glitazone) for Type 2 Diabetes, Jul. 14, 2014.
Silva-Abreu et al., "Thiazolidinedione as an alternative to facilitate oral administration in geriatric patients with Alzheimer's disease," Europ. J. of Pharm. Sci., 129:173-180, 2019.

* cited by examiner

*Primary Examiner* — Melissa S Mercier
(74) *Attorney, Agent, or Firm* — Gavrilovich, Dodd & Lindsey LLP

(57) ABSTRACT

The disclosure relates to methods and compositions to treat an eosinophilic disease or disorder. More particularly, the disclosure provides methods and compositions for treating eosinophilic esophagitis.

11 Claims, 9 Drawing Sheets

Specification includes a Sequence Listing.

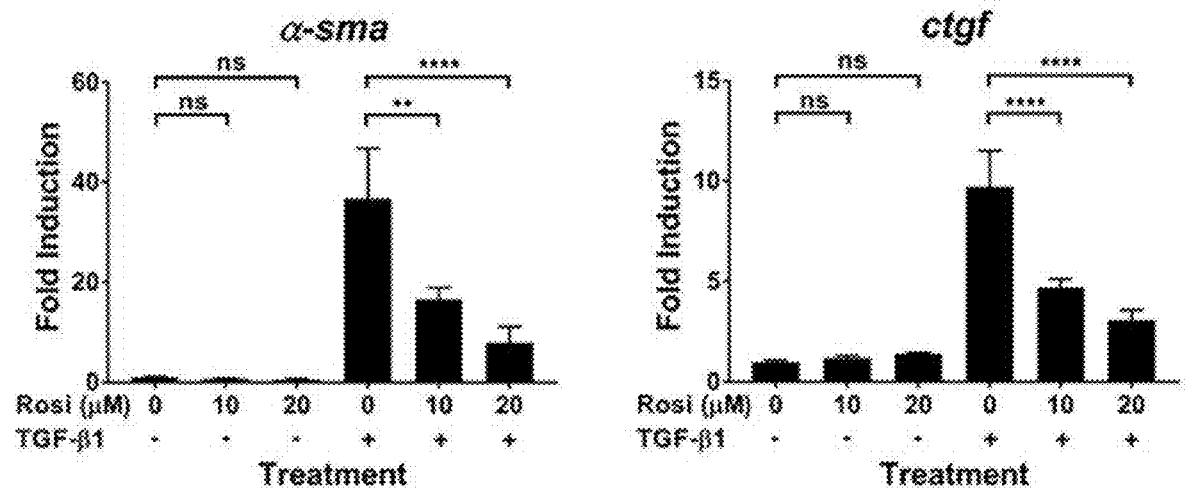
FIG. 1F
FIG. 1G
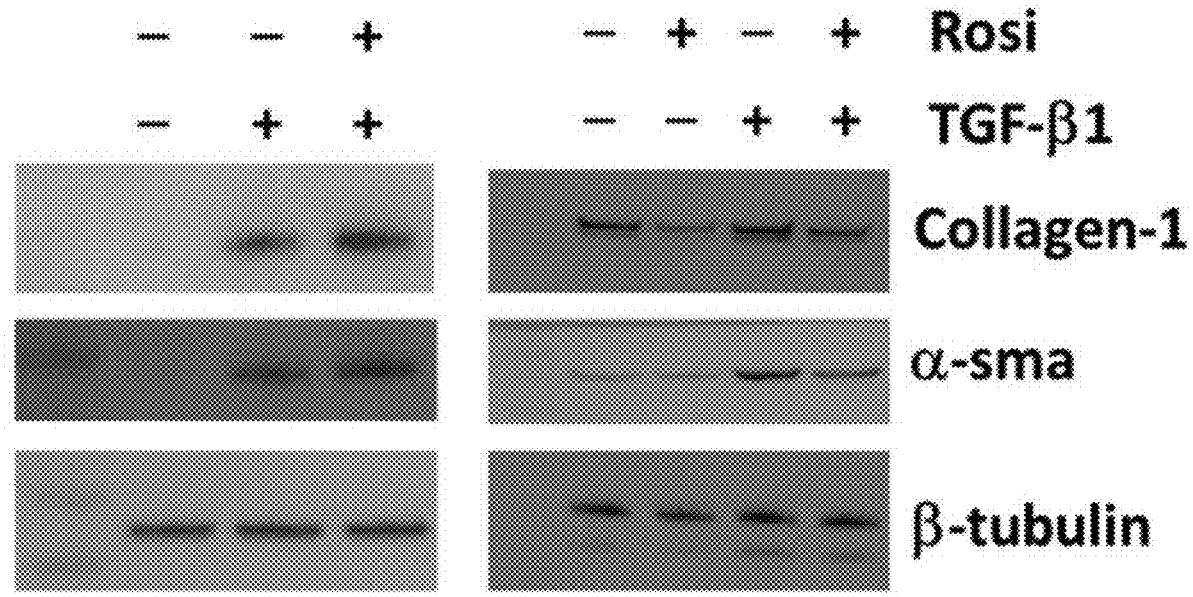
FIG. 2A

SEQUENCE LISTING

```
Sequence total quantity: 10
SEQ ID NO: 1             moltype = DNA   length = 19
FEATURE                  Location/Qualifiers
source                   1..19
                         mol_type = other DNA
                         organism = synthetic construct
SEQUENCE: 1
ccgaccgaat gcagaagga                                                 19

SEQ ID NO: 2             moltype = DNA   length = 21
FEATURE                  Location/Qualifiers
source                   1..21
                         mol_type = other DNA
                         organism = synthetic construct
SEQUENCE: 2
acagagtatt tgcgctccga a                                              21

SEQ ID NO: 3             moltype = DNA   length = 19
FEATURE                  Location/Qualifiers
source                   1..19
                         mol_type = other DNA
                         organism = synthetic construct
SEQUENCE: 3
cagccgcttc acctacagc                                                 19

SEQ ID NO: 4             moltype = DNA   length = 25
FEATURE                  Location/Qualifiers
source                   1..25
                         mol_type = other DNA
                         organism = synthetic construct
SEQUENCE: 4
ttttgtattc aatcactgtc ttgcc                                          25

SEQ ID NO: 5             moltype = DNA   length = 17
FEATURE                  Location/Qualifiers
source                   1..17
                         mol_type = other DNA
                         organism = synthetic construct
SEQUENCE: 5
accaatgaca acgcctc                                                   17

SEQ ID NO: 6             moltype = DNA   length = 20
FEATURE                  Location/Qualifiers
source                   1..20
                         mol_type = other DNA
                         organism = synthetic construct
SEQUENCE: 6
agattttggg agtacggatg                                                20

SEQ ID NO: 7             moltype = DNA   length = 21
FEATURE                  Location/Qualifiers
source                   1..21
                         mol_type = other DNA
                         organism = synthetic construct
SEQUENCE: 7
tggtatcgtg gaaggactca t                                              21

SEQ ID NO: 8             moltype = DNA   length = 21
FEATURE                  Location/Qualifiers
source                   1..21
                         mol_type = other DNA
                         organism = synthetic construct
SEQUENCE: 8
atgccagtga gcttcccgtt c                                              21

SEQ ID NO: 9             moltype = DNA   length = 19
FEATURE                  Location/Qualifiers
source                   1..19
                         mol_type = other DNA
                         organism = synthetic construct
SEQUENCE: 9
ttagatgaca gcgacttgg                                                 19
```

| | |
|---|---|
| SEQ ID NO: 10 | moltype = DNA length = 20 |
| FEATURE | Location/Qualifiers |
| source | 1..20 |
| | mol_type = other DNA |
| | organism = synthetic construct |
| SEQUENCE: 10 | |
| gtagcaggtt gtcttgaatg | 20 |

COMPOSITIONS AND METHODS FOR TREATING EOSINOPHILIC DISORDERS

CROSS REFERENCE TO RELATED APPLICATIONS

This application is a divisional of U.S. application Ser. No. 16/894,784, filed Jun. 6, 2020 (now U.S. Pat. No. 1,157,664), which application claims priority to U.S. Provisional Application No. 62/858,951, filed Jun. 7, 2019, the disclosures of which are incorporated herein by reference in their entirety.

STATEMENT REGARDING FEDERALLY SUPPORTED RESEARCH

This invention was made with government support under AI092135, TR001114, TR001112, and AI135034 awarded by the National Institutes of Health. The government has certain rights in the invention.

FIELD OF THE INVENTION

The invention relates to the methods and compositions for treating eosinophilic disorders.

INCORPORATION BY REFERENCE OF SEQUENCE LISTING

Accompanying this filing is a Sequence Listing entitled "00015-370002.xml", created on Jan. 4, 2023 and having 9,958 bytes of data, machine formatted on IBM-PC, MS-Windows operating system. The sequence listing is hereby incorporated herein by reference in its entirety for all purposes.

BACKGROUND

Esophageal inflammation disorders are gaining increased recognition in both adults and children. One example is eosinophilic esophagitis (EE or EoE), which is an emerging and fast-growing disorder characterized by high levels of eosinophils in the esophagus, as well as basal zone hyperplasia and esophageal remodeling that includes fibrosis and smooth muscle dysfunction leading to complications of strictures and food impactions. EoE is thought to be provoked, in at least a subset of patients, by food allergies or airborne allergen exposure. EoE diagnosis is often associated with other hypersensitivity disorders, including asthma, rhinitis, and other food and aeroallergen inhalant sensitivities. Diagnosis is often made, e.g., in young children and depends on the finding of 15 or more eosinophils per high power field (eos/hpf) within esophageal mucosal biopsies.

The disorder may present with reflux-like symptoms, pain and dysphagia, clinical symptoms similar to the presentation of gastroesophageal reflux disease ("GERD"). Symptoms of EoE may include, for example, one or more of the following: abdominal pain, chest pain, choking, difficulty swallowing, failure to thrive, nausea, reflux, vomiting, and weight loss. In one series, 15% of EoE patients had concurrent developmental delay.

Although EoE is becoming more frequently diagnosed throughout developing countries many aspects of the disease remain unclear including its etiology, natural history and optimal therapy. Symptoms of EoE often mimic those of GERD and include vomiting, dysphagia, pain and food impaction.

SUMMARY

The disclosure provides methods and compositions for treating eosinophilic inflammatory diseases and fibrosis. The methods and composition use local or system administration of thiazolidinediones to a subject having fibrosis resulting from an inflammatory eosinophilic disease or disorder. The disclosure demonstrates that TZDs inhibit and reduce fibrotic formation.

The disclosure provides a composition comprising one or more thiazolidinediones (TZDs) in an oral viscous formulation. In another embodiment, the TZDs are selected from rosiglitazone, pioglitazone, lobeglitazone and a combination thereof. In another or further embodiment, the composition further comprises a corticosteroid. In a further embodiment, the corticosteroid comprises budesonide.

The disclosure provides a method of treating an eosinophilic disease or disorder resulting comprising inflammation and resulting in fibrosis, the method comprising administering a composition of the disclosure, wherein the composition inhibits or reduces fibrosis.

The disclosure provides a method comprising treating eosinophilic esophagitis in a subject having fibrosis, the method comprising administering locally or systemically one or more thiazolidinediones in an amount to inhibit or reduce fibrosis. In another embodiment, the method further comprises administering a local corticosteroid to the esophagus or gastrointestinal tract.

The disclosure provides a method of preventing or alleviating esophageal inflammation and fibrosis in an individual comprising orally administering to said individual a pharmaceutical composition comprising a corticosteroid and one or more thiazolidinediones (TZDs) in association with at least one viscosity enhancing excipient. In another embodiment, the pharmaceutical composition further comprises a liquid vehicle. In another embodiment, the pharmaceutical composition is a suspension comprising corticosteroid microparticles. In still another embodiment, the pharmaceutical composition is in the form of a dissolvable tablet, a dissolvable wafer, or a dissolvable capsule. In another embodiment, the pharmaceutical composition is administered once a day, twice a day, or three times a day. In yet another embodiment, the pharmaceutical composition is administered no more than once a day. In yet another embodiment, the corticosteroid is a topical corticosteroid. In a further embodiment, the corticosteroid is Budesonide. In still another embodiment, the one or more TZDs are selected from the group consisting of rosiglitazone, pioglitazone and a combination thereof. In another embodiment, the viscosity enhancing excipient is selected from the group consisting of lactose, sucrose, sucralose, maltodextrin, dextrose, mannitol, sorbitol, honey, maize starch, wheat starch, rice starch, potato starch, gelatin, gum tragacanth, methyl cellulose, hydroxypropylmethyl-cellulose, a carboxymethyl cellulose (CMC), sodium carboxymethyl-cellulose (NaCMC), polyvinylpyrrolidone (PVP: povidone), and combinations thereof. In yet another embodiment, the esophageal inflammation is eosinophilic esophagitis. In still another embodiment, the individual has been diagnosed with a disease or condition selected from the group consisting of eosinophilic esophagitis, inflammatory bowel diseases involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, and post-surgery inflammation.

The disclosure provides a method of treating an eosinophilic inflammatory disease or disorder that comprising inflammation and fibrosis, the method comprising administering at least one corticosteroid and at least one thiazolidinedione (TZD) simultaneously or sequentially. In another embodiment, the TZD is administered systemically and the corticosteroid is administered locally. In another embodiment, the eosinophilic inflammatory disease or disorder is eosinophilic esophagitis.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an embodiment of the invention. Also, aspects described as a genus or selecting a member of a genus, should be understood to embrace combinations of two or more members of the genus. Variations of the invention defined by such amended paragraphs also are intended as aspects of the invention.

BRIEF DESCRIPTION OF THE FIGURES

FIG. 1A-G shows EoE-derived primary esophageal fibroblasts respond selectively to rosiglitazone. Human primary esophageal fibroblasts (FBL) derived from normal donors or EoE patients were stimulated with rosiglitazone (20 µM for panels A-E; 10 µM or 20 µM for panels F-G) or vehicle (DMSO) for 3 hours and then treated with TGF-β1 (TGF, 5 ng/mL) for 24 hours in the presence of vehicle or rosiglitazone. mRNA expression was determined by real-time qPCR and expressed as mean±s.d. Med, medium; rosi, rosiglitazone; ns, not significant; *, $p<0.05$; , $p<0.01$; *, $p<0.001$; ****, $p<0.0001$. Results are representative of >3 separate experiments.

FIG. 2A-I shows EoE-derived primary esophageal fibroblasts selectively respond to rosiglitazone: protein analysis. Human primary esophageal fibroblasts from normal donors or patients with EoE were stimulated with vehicle (dimethylsulfoxide) or rosiglitazone (20 µM) for 3 hours and then treated with TGF-β1 (5 ng/mL) for 24 hours in the presence or absence of rosiglitazone. A representative blot is shown (A). Protein expression of α-sma and collagen-1 was analyzed and quantified in 3 normal controls and in 7-8 patients with EoE (B-I). (E and I) Panels represent quantification of biological replicates in a patient with EoE. EoE, eosinophilic esophagitis; Med, medium; ns, not significant; rosi, rosiglitazone. *$P<0.05$; $P<0.01$; **$P<0.0001$.

DETAILED DESCRIPTION

Figure 1A:
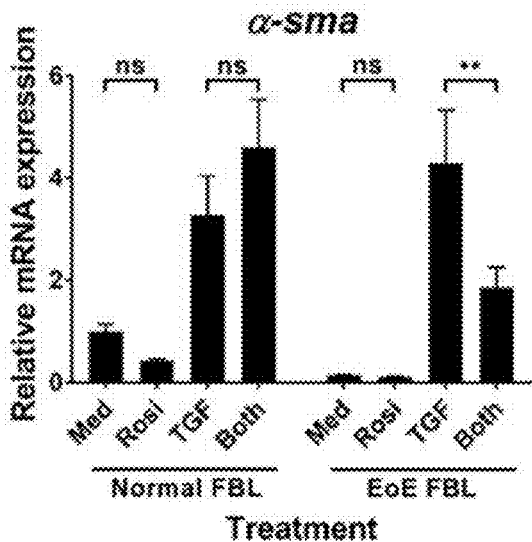
Figure 1B:
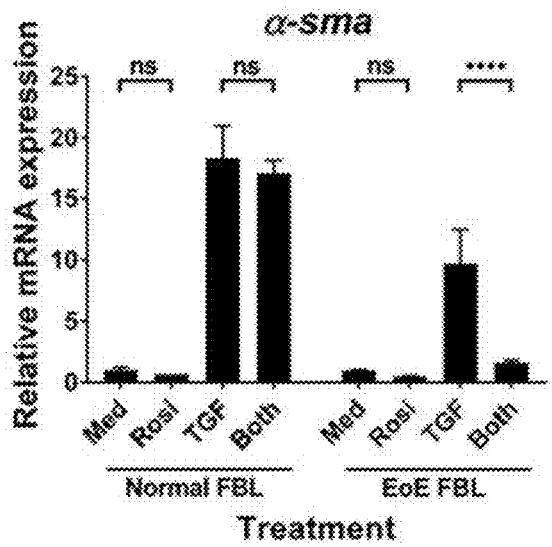
Figure 1C:
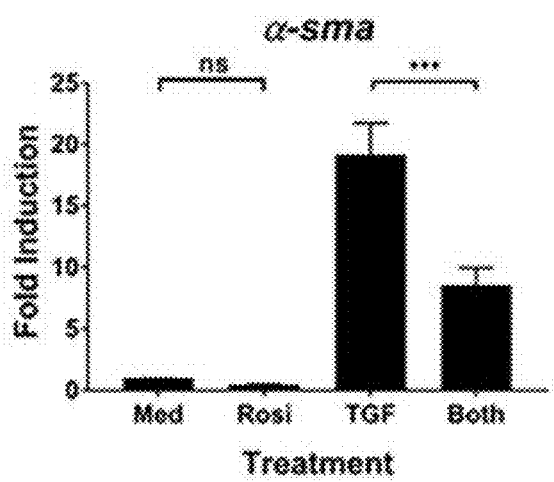
Figure 1D:
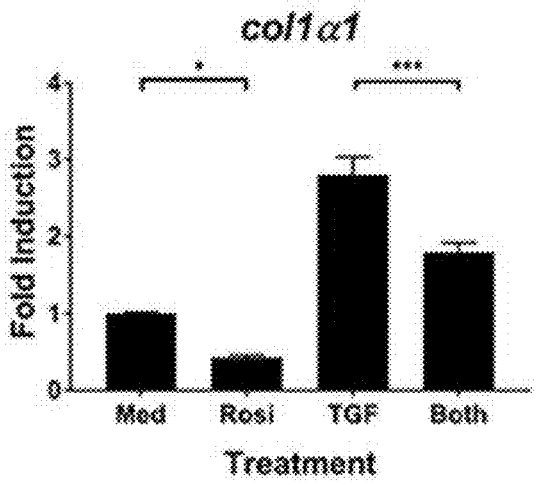

As used herein and in the appended claims, the singular forms "a," "an," and "the" include plural referents unless the context clearly dictates otherwise. Thus, for example, reference to "a protein" includes a plurality of such proteins and reference to "a patient" includes reference to one or more patients and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and products, the exemplary methods, devices and materials are described herein.

The documents discussed above and throughout the text are provided solely for their disclosure prior to the filing date of the present application. Nothing herein is to be construed as an admission that the inventors are not entitled to antedate such disclosure by virtue of prior disclosure. Each document is incorporated by reference in its entirety with particular attention to the disclosure for which it is cited.

As used herein, the term "subject" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender. In various embodiments the subject is human. In some embodiments, the subject is a human child having an age of 16 years or less. Administration of a therapeutic described herein to a child having an age of 16, 15, 14, 13, 12, 11, 10, 9, 8, 7, 6, 5, 4, 3, 2, 1 or younger is specifically contemplated. In some embodiments, the subject is 12-17 years old, 12-16 years old, or 12-15 years old, 2-9 years old, or 10-18 years old. In some embodiments, the subject is an adult human. In other embodiments, the subject is 18 or more years old. In some embodiments, the subject is an infant human of about 1-12 months of age. In another embodiment, the subject is a toddler of about 1-3 years of age. In yet another embodiment, the subject is a human child of primary school age (e.g., about 4-11 years of age). In still another embodiment, the subject is an adolescent of about 12-18 years of age.

As mentioned above Eosinophilic Esophagitis (EoE) is now a relatively common disorder which, up to about 20 yrs years ago, was rarely reported. Now, between 1 in 500 to 1 in 1000 people are believed to suffer with this disorder. Eosinophilic esophagitis (EoE) is a chronic, T-helper 2 (Th2)-mediated, antigen-driven disease of the esophagus. Pathological tissue remodeling results in esophageal stricturing, rigidity, and fibrostenosis that manifest clinically as dysphagia and food impactions. Unbridled or sub-optimally controlled EoE-associated inflammation can lead to persistent or recurrent esophageal strictures. In its earlier stages, esophageal inflammation and remodeling are coupled in EoE. However, over time, fibrosis and rigidity can dissociate from inflammation in EoE patients. Diminished esophageal distensibility, rather than the degree of esophageal eosinophilia or mucosal inflammation, is a predictor for EoE-related food impaction in adult EoE. Esophageal fibrosis may ultimately lead to esophageal stricture formation significant symptoms and impact to quality of life.

Submucosal fibrosis is a prominent histologic feature of EoE and other eosinophilic disorders. Medical and diet elimination therapies can reverse esophageal subepithelial fibrosis in pediatric EoE and improve esophageal distensibility in adults. While most children and many adults respond to standard EoE therapy, disease response is often not absolute nor sustained. Subgroups of patients, such as those with a narrowed esophagus, are often resistant to standard EoE anti-inflammatory therapies. Given studies that demonstrate that a physically rigid extracellular environment induces mechanotransduction and alters esophageal smooth muscle and fibroblast cell size and gene expression, there are likely to be in vivo mechanisms that drive inflammation-independent esophageal remodeling. Furthermore, persistent activation of fibroblasts can persist even after resolution of inflammation. These issues support a significant unmet need for novel anti-fibrotic therapies in EoE.

Esophageal diseases including Eosinophilic Esophagitis (EoE) are associated with fibrosis and tissue remodeling that leads to eventual organ dysfunction. It has been shown that eosinophils have been found to be increased or pathologically present in various conditions, including skin and subcutaneous disorders, pulmonary conditions, gastrointestinal diseases, neurologic disorders, cardiac conditions and renal disease. Exemplary skin and subcutaneous disorders in which eosinophils have been found to be pathologically present include, but are not limited to, atopic dermatitis (eczema), bullous pemphigoid, *Pemphigus vulgaris*, dermatitis herpetiformis, drug-induced lesions, urticaria, eosinophilic panniculitis, angioedema with eosinophilia, Kimura's disease, Shulman's syndrome, Well's syndrome, eosinophilic ulcer of the oral mucosa, eosinophilic pustular folliculitis, and recurrent cutaneous necrotizing eosinophilic vasculitis. (See, e.g., Simon et al. J Allergy Clin Immunol. 2010 July; 126(1): 3-13).

Exemplary pulmonary conditions associated with pathologically present eosinophils include, but are not limited to, drug/toxin-induced eosinophilic lung disease, Loeffler's syndrome, allergic brochopulmonary aspergillosis, eosinophilic pneumonia, Churg-Strauss syndrome, eosinophilic granuloma and pleural eosinophilia.

Exemplary gastrointestinal diseases associated with pathologically present eosinophils include, but are not limited to, gastroesophageal reflux, parasitic infections, fungal infections, *Helicobacter pylori* infections, inflammatory bowel disease (ulcerative colitis and Crohn's disease), food allergic disorders, protein-induced enteropathy and protein-induced enterocolitis, allergic colitis, celiac disease, *Pemphigus vegetans* (MR) and primary eosinophilic esophagitis, gastroenteritis, and colitis.

Exemplary neurologic disorders associated with pathologically present eosinophils include, but are not limited to, organizing chronic subdural hematoma membranes, central nervous system infections, ventriculoperitoneal shunts, and drug-induced adverse reactions.

Exemplary cardiac conditions associated with pathologically present eosinophils include, but are not limited to, Secondary to systemic disorders such as the hypereosinophilic syndrome or the Churg-Strauss syndrome, heart damage has been reported. It is also known that certain congenital heart conditions (such as septal defects, aortic stenosis) are associated with increased levels of eosinophils in the blood.

Exemplary renal diseases associated with pathologically present eosinophils include, but are not limited to, interstitial nephritis and eosinophilic cystitis.

Although inflammation is considered the trigger for fibrosis, the inflammation-fibrosis connection may become uncoupled. Over time, florid inflammation can diminish while fibrosis continues to progress due to dysregulated tissue remodeling, resulting in further tissue dysfunction. Standard treatments such as topical corticosteroids and antigen elimination diets resolve inflammation but have variable effects on remodeling, likely depending on the patient phenotype, genotype, and disease stage. Commonly used medications such as topical corticosteroids can reduce the onset of strictures and food impactions with chronic use in adults and children, especially when the disease duration is short and when fibrosis is linked to inflammation. However, many patients, especially adults, are diagnosed following long-standing disease, and thus, can have uncoupling of inflammation and rigidity, and might not respond optimally to standard EoE therapy. While topical corticosteroids or food elimination can reverse histologic fibrosis and epithelial remodeling, as well as esophageal rigidity in subsets of children and adults, resolution of eosinophilia can be incomplete even in clinical responders, leaving non-responders and even some corticosteroid-responsive patients vulnerable to potential esophageal narrowing. In addition, the fibrostenotic esophagus is often resistant to medical treatments. This situation leaves a pressing need for novel isolated or adjuvant anti-fibrotic therapies.

The disclosure describes compositions and method of using corticosteroids and Thiazolidinediones in combination to treat eosinophilic diseases and disorders (e.g., EoE) targeting both the inflammatory response and the fibrotic response.

In some embodiments, corticosteroids are selected from, by way of non-limiting example, aclometasone, amcinomide, beclometasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluticasone, fluticasone propionate, fuprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, remexolone, tixocortol, triamcinolone and ulobetasol, and combinations, pharmaceutically acceptable salts and esters thereof. In certain embodiments, the corticosteroids used in the disclosure comprise topical steroids including, for example, budesonide. Budesonide is a synthetic corticosteroid which has been effective for the treatment of inflammatory diseases of the gastrointestinal tract such as EoE, Crohn's disease and ulcerative colitis. The chemical name of budesonide is 16,17-(butylidenebis(oxy))-11,21-dihydroxy-, (11-β,16-α)-pregna-1,4-diene-3,20-dione, and its chemical structure is:

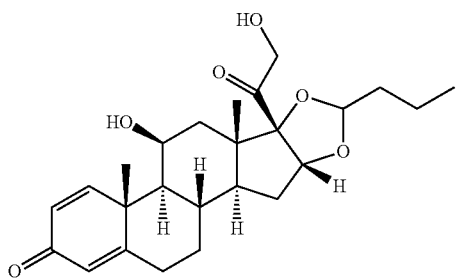

Corticosteroids (e.g., budesonide) when administered in oral form, in a formulation with increased coating (e.g., viscosity and/or mucoadhesive) characteristic, has been shown to be effective at reducing the inflammation of the esophagus.

Thiazolidinediones (TZDs), are a class of compounds which work by enhancing insulin action and promoting glucose utilization in peripheral tissue. TZDs include compounds known in the art as "TZD derivatives." TZDs have no effect on insulin secretion. They apparently work by enhancing insulin action and thus promoting glucose utilization in peripheral tissues, possibly by stimulating nonoxidative glucose metabolism in muscle, and suppressing gluconeogenesis in the liver. The chemical compounds that comprise the Thiazolidinedione (TZD) class of compounds is exceptionally large. See, for example, Bowen, et al. Metabolism 40:1025 (1991); Chang, et al Diabetes 32:630 (1983); Colca, et al. Metabolism 37:276 (1988); Diani, et al. Diabetologia 27:225 (1984); Fujita, et al. Diabetes 32:804 (1983); Fujiwara, et al. Diabetes 37:1549 (1988). Exemplary of the family of thiazolidinediones are troglitazone, ciglitazone, pioglitazone (see U.S. Pat. Nos. 4,687,777 and 4,287,200), englitazone, CS-045[(±)-5[4-(6-hydroxy-2,5,7,8-tetramethylchroman-2-YL-methoxy) benzyl]-2,4-thiazolidinedione], TZD 300512, and BRL 49653. The thiazolidinediones (TZD), such as the FDA-approved antidiabetic drugs rosiglitazone and pioglitazone, function as agonists for the ligand-activated nuclear receptor peroxisome proliferator-activated receptor-y (PPAR-γ). PPAR-γ is a key regulator of lipid and glucose metabolism expressed on multiple cell types that can have anti-fibrotic, pro-adipogenic, and anti-inflammatory effects in structural and immune cells. Rosiglitazone is effective in the treatment of mild to moderately active ulcerative colitis. Pioglitazone, a more clinically favorable TZD, improves liver fibrosis in adults with nonalcoholic steatohepatitis (NASH), achieving resolution of NASH in up to 51% of patients. In addition, pioglitazone was reported to be well tolerated and had no major drug-related adverse events when compared to placebo. PPAR gamma agonists such as rosiglitazone and pioglitazone, metformin, pentoxyfylline, vitamin E, selenium, omega-3 fatty acids and betaine are of particular interest.

Given the natural trajectory of EoE towards pathologic remodeling with fibrosis, it was hypothesized that TZDs might decrease fibrotic gene and protein expression in esophageal fibroblasts. The disclosure demonstrates the differential expression of PPAR-γ in EoE versus normal esophagi and the ability of the TZDs to reduce fibrotic and myofibroblast gene and protein expression in EoE-derived esophageal fibroblasts, setting forth their use as therapeutic agents to treat the fibrotic diseases including fibrosis of the esophagus in EoE.

The disclosure demonstrates the effects of the TZDs (exemplified by rosiglitazone and pioglitazone) on esophageal fibroblast expression of markers of fibrosis and myofibroblast transformation. While normal esophageal fibroblasts were relatively resistant to the effects of the TZDs at the concentrations used herein, up to 20 μM, fibroblasts derived from EoE biopsies were sensitive to the TZDs. The TZDs antagonized the non-canonical TGF-β1 pathway leading to diminished phosphorylated p38 levels, while sparing the canonical TGF-β1-mediated Smad2/3 phosphorylation pathway. In addition, the TZDs (e.g., rosiglitazone) had distinct effects on cultured EoE esophageal fibroblasts as compared with budesonide. As such, the TZD class of drugs can function in vivo as adjuvant anti-fibrotic therapies in patients that have advanced, strictured, or steroid-resistant fibrotic disease such as EoE.

The TZDs activate PPAR-γ to promote anti-inflammatory and anti-fibrotic effects. Interestingly, there was up-regulation of PPAR-γ expression at the transcript and protein levels in EoE esophageal fibroblasts and biopsies, respectively, suggesting a protective compensatory mechanism to protect the esophagus from further pathological remodeling. This likely reflects the wound healing and protective nature of fibroblasts as they attempt to down-regulate fibrosis and potentially promote tissue softening. This likely provides an opportunity to use an endogenously occurring wound healing mechanism via PPAR-γ agonism. The EoE epithelium and subepithelium had increased expression of PPAR-γ in the severe active state, with little to no detection of PPAR-γ expression in the normal state. Similarly, consistent with the concept of EoE being akin to an asthmatic type pathogenesis in the esophagus, PPAR-γ expression is elevated in the airway epithelium of asthma and allergic airway disease.

PPAR-γ deficiency in airway epithelial cells exacerbated murine allergic airway disease, and PPAR-γ activation via agonist nebulization was protective, resulting in reduced airway hyper-reactivity, allergic inflammation, and eosinophil activation. Furthermore, PPAR-γ agonism decreased airway collagen deposition and TGF-β expression in a murine asthma model. The data suggest that EoE patients with active disease may have higher PPAR-g expression and thus would be potential clinical candidates for additional therapies such as the TZDs. As such, TZD compounds may be useful as therapeutic options to preferentially target diseased tissues in EoE while potentially sparing healthy tissues.

PPAR-γ-positive CD4+ T cells were recently identified in EoE tissues. PPAR-γ has been described to promote Th2 immune responses. PPAR-γ was reported to promote Th2 cells that express IL-9, a cytokine thought to be pathogenic in EoE. However, PPAR-γ inhibited T cell activation and CD4$^+$ T cell effector function, including inhibition of IL-4 production. Furthermore, PPAR-γ positively regulated the tissue accumulation, phenotype and function of regulatory T-cells to suppress tissue inflammation. Pioglitazone administration resulted in an enrichment of tissue regulatory T-cells. The expression of PPAR-γ in T cells was protective against experimental colitis. PPAR-γ suppressed eosinophilic activation and mast cell maturation and activation. Activation of the PPAR-γ pathway could provide anti-inflammatory and antifibrotic benefits in patients with EoE.

The EoE epithelium and sub-epithelium also had increased expression of PPAR-γ in the severe, active state, with little to no detection of PPAR-γ expression in the normal state. Similarly, consistent with the concept of EoE being akin to an asthmatic type pathogenesis in the esophagus, PPAR-γ expression is elevated in the airway epithelium of asthma and allergic airway disease. PPAR-γ deficiency in airway epithelial cells exacerbated murine allergic airway disease. PPAR-γ activation via agonist nebulization was protective, resulting in reduced airway hyper-reactivity, allergic inflammation, and eosinophil activation. The biopsy data suggest that patients with severe disease may have higher PPAR-γ expression and thus would be potential clinical candidates for additional therapies such as TZDs. As such, TZD are useful as therapeutic options to preferentially target inflamed tissues in EoE while potentially sparing healthy tissues.

TZDs have been demonstrated to improve ulcerative colitis and NASH. Early progress in the development of TZDs for ulcerative colitis, however, was hampered by the potential cardiotoxicity profile of rosiglitazone, although the myocardial infarction risk was subsequently disproven. In contrast to rosiglitazone, pioglitazone has been shown to have a cardioprotective effect. In addition, given the inherent antifibrotic and proadipogenic effects of the TZDs, there is a concern for an effect on bone mineral density and the potential risk for fractures. However, recent placebo-controlled long-term studies evaluating pioglitazone for NASH reported that the drug was well tolerated, without major drug-related adverse events. It is of note that most of these studies used a higher dose of pioglitazone, ranging from 30 mg to 45 mg daily. A lower dose of pioglitazone of 7.5 mg orally daily has been proposed and may serve useful. Previous studies in ulcerative colitis used up to 8 mg per day with favorable clinical activities. In addition to dose reduction, it is possible that topical delivery of the TZDs might achieve directed beneficial therapeutic effects while sparing some of the potential adverse drug effects when given systemically. For example, topical delivery of rosiglitazone as an enema improved ulcerative colitis. In addition, a locally active, novel topical PPAR-γ agonist AS002 was recently developed and was demonstrated to induce PPAR-γ in human colonic biopsies stimulated ex vivo. In mice, AS002 prevented and reversed colitis in vivo in a murine model of colitis. The combination of reduced dosing and topical esophageal delivery of the TZDs might allow for directed therapy to the esophagus while minimizing potential systemic adverse effects.

Accordingly, the disclosure provides in one embodiment, a method of treating, preventing or alleviating allergic or caustic inflammation of the gastrointestinal tract, including, by way of non-limiting example, the esophagus, comprising orally administering a corticosteroid (e.g., budesonide) compositions described herein prior to, simultaneously with or following administration of one or more TZDs to a subject. In certain embodiments, an oral dosage form comprises a liquid vehicle and is formulated as, e.g., a slurry, suspension, syrup, solution, dispersion, etc. In one embodiment, the composition further comprises one or more thiazolidinediones (TZDs). In another embodiment, a method of treating the subject comprises administering to a subject in need of treatment for an eosinophilic disease or disorder a composition comprising a corticosteroid such as budesonide and one or more TZDs in an oral viscous solution. In another embodiment, the disclosure provides a composition that comprises corticosteroid such as budesonide and one or more TZDs in a formulation for topical or mucosal delivery. In yet another embodiment, the disclosure provides a method of treating a subject with an eosinophilic disease or disorder such as EoE with an orally viscous or topical budesonide and administering a systemic formulation of one or more TZDs or a PPAR-γ agonist.

In some embodiments, the inflammation treated by the methods and compositions described herein is associated with eosinophilic inflammation. In some embodiments, individuals (e.g., patients) to be treated with compositions described herein include those that have been diagnosed with eosinophilic esophagitis, an inflammatory bowel disease involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, or post-surgery inflammation. In one non-limiting example, the patient has eosinophilic esophagitis. In some embodiments, the patient is an adult. In other embodiments, the patient is a child or infant. In various aspects, a patient is a child or infant less than 19 years old, less than 16 years old, less than 12 years old, less than 8 years old, less than 6 years old, less than 4 years old, less than 2 years old, 2-18 years old, or 2-19 years old. In any of the foregoing embodiments the individuals (e.g., patients) are administered one or more TZDs in an amount effective to inhibit fibrosis and/or decrease fibrosis resulting from the disease or disorder.

In some embodiments, a composition is in a unit dose formulation for oral administration to a patient. In some embodiments, a unit dose of the corticosteroid and/or the one or more TZDs is administered from a metered dose device. In some embodiments, the metered dose device delivers a metered unit dose of a composition described herein to the mouth or throat of an individual in need thereof. In certain embodiments, the metered dose device is a metered inhaler, which is utilized to administer a metered unit dose to the mouth or throat of an individual (the individual swallows rather than inhales the metered unit dose). In some embodiments, a composition or unit dose described herein is administered as a nebulized composition, an aerosolized composition, an emulsion, a solution, a suspension, a syrup, a slurry, a dispersion, a colloid, a dissolving tablet, a dissolving wafer, a capsule, a gel capsule, a semi-solid, a solid forma gel, a gel matrix, a cream, a paste, or the like. In certain aspects, about 0.01 mg to about 20 mg, about 0.01 mg to about 15 mg, or about 0.01 mg to about 10 mg (e.g., about 0.1-10 mg, about 0.25-5 mg, about 0.25-2.5 mg, about 1-2 mg or about 2-3 mg, about 0.25 mg to about 6 mg, about 0.5 mg to about 6 mg of each active ingredient (i.e., the corticosteroid and one or more TZDs) per day or per dose is administered to an individual. In some embodiments, the corticosteroid and/or one or more TZDs is present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg, about 0.5 mg to about 2 mg, about 1 to about 2 mg, about 1 mg, or about 2 mg). In some embodiments, the amount of corticosteroid and one or more TZDs administered daily or in a unit dose is between about 0.5 mg and about 3 mg, between about 0.5 mg and about 4 mg, or between about 0.35 mg and about 4 mg each. In other embodiments, the amount of corticosteroid and one or more TZDs present in a unit dose or administered daily is between about 1 and about 3 mg, or between about 1 and about 2 mg, or between about 2 and about 3 mg for each active ingredient (i.e., the corticosteroid or one or more TZDs).

In certain embodiments, about 0.05 mg to about 50 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) of each of the corticosteroid and one or more TZDs are administered per day or per dose to a patient. In some embodiments, the corticosteroid is present in a unit dose in an amount of between about 0.25 mg and about 5 mg. In some embodiments, the amount of corticosteroid administered daily or in a unit dose is between about 0.5 mg and about 3 mg. In other embodiments, the amount of corticosteroid present in a unit dose or administered daily is between about 1 and about 3 mg, or between about 1 and about 2 mg, between about 0.5 mg and about 4 mg, between about 0.35 mg and about 4 mg, or between about 2 and about 3 mg. In some embodiments, the one or more TZDs is present in a unit dose in an amount of between about 0.25 mg and about 5 mg. In some embodiments, the amount of corticosteroid administered daily or in a unit dose is between about 0.5 mg and about 3 mg. In other embodiments, the amount of one or more TZDs present in a unit dose or administered daily is between about 1 and about 3 mg, or between about 1 and about 2 mg, between about 0.5 mg and about 4 mg, between about 0.35 mg and about 4 mg, or between about 2 and about 3 mg.

Provided in certain embodiments herein is a method of treating allergic or caustic inflammation and fibrosis of the gastrointestinal tract (e.g., of the esophagus) in an individual comprising coating an inflamed and/or fibrotic portion of the gastrointestinal tract (e.g., a portion or a substantial portion of the esophagus) of an individual with an effective amount of a pharmaceutical composition. In specific embodiments, the pharmaceutical composition comprising a therapeutically effective amount of a topically active corticosteroid and/or an effective amount of an anti-fibrotic amount of one or more TZDs. In certain embodiments, the pharmaceutical composition further comprises a coating agent (e.g., a mucoadhesive agent and/or a viscosity enhancing agent). In some embodiments, the inflamed and/or fibrotic portion of the gastrointestinal portion is at least partially coated, or substantially coated. In certain embodiments, the effective amount of the pharmaceutical composition is an amount sufficient to coat the esophagus (e.g., a volume as set forth herein). In certain embodiments, the allergic or caustic inflammation and/or fibrotic portion of the gastrointestinal tract is the esophagus and the composition at least partially coats the esophagus (including all or part of the inflamed and/or fibrotic portions of the esophagus). In specific embodiments, the inflammation and/or fibrosis of the gastrointestinal tract is associated or results from allergic inflammation of the esophagus (e.g., eosinophilic esophagitis).

The methods are also useful for treating, preventing or alleviating symptoms of inflammation and/or fibrosis associated with other diseases or conditions of the gastrointestinal tract, for example, the upper gastrointestinal tract, where it is beneficial to target a particular target site, rather than provide systemic therapy. Also provided herein are pharmaceutical compositions useful in the methods of the present application. As used herein, inflammation symptoms and/or fibrosis associated with a disorder or disease disclosed herein includes inflammation symptoms and/or fibrosis associated with, caused by and/or resulting from the disorder or disease.

In certain embodiments, the disclosure provides a method of treating allergic or caustic gastrointestinal inflammation and/or fibrosis in an individual comprising orally administering a pharmaceutical composition of the disclosure to an individual in need thereof and delivering the pharmaceutical composition to an inflamed and/or fibrotic portion of the gastrointestinal tract, wherein the pharmaceutical composition comprises a topically active corticosteroid and one or more TZDs. In further embodiments, upon delivery of the pharmaceutical composition to the inflamed and/or fibrotic portion of the gastrointestinal tract, the pharmaceutical composition coats the inflamed and/or fibrotic portion of the gastrointestinal tract. In further embodiments, coating of the inflamed and/or fibrotic portion of the gastrointestinal tract provides prolonged exposure of the inflamed and/or fibrotic portion of the gastrointestinal tract to the pharmaceutical composition. In still further embodiments, prolonged exposure of the inflamed and/or fibrotic portion of the gastrointestinal tract to the pharmaceutical composition provides increased local delivery of the corticosteroid and one or more TZDs. In some embodiments, increased local delivery of the corticosteroid and one or more TZDs to a surface of the gastrointestinal tract decreases undesired systemic absorption of the corticosteroid and one or more TZDs. In some embodiments, the inflamed and/or fibrotic portion of the gastrointestinal portion is at least partially coated, or substantially coated. In certain embodiments, the effective amount of the pharmaceutical composition is an amount sufficient to coat the esophagus (e.g., a volume as set forth herein). In certain embodiments, the allergic or caustic inflammation and/or fibrosis of the gastrointestinal tract is the esophagus and the composition at least partially coats the esophagus (including all or part of the inflamed and/or fibrotic portion of the esophagus). In specific embodiments, the inflammation and/or fibrosis of the gastrointestinal tract is due to or results from allergic inflammation of the esophagus (e.g., eosinophilic esophagitis).

In some embodiments, provided herein is a method of reducing systemic exposure to a corticosteroid in an individual being treated for allergic or caustic gastrointestinal inflammation and/or fibrosis, the method comprising orally administering a pharmaceutical composition and coating an inflamed and/or fibrotic portion of the gastrointestinal tract with the pharmaceutical composition, wherein the pharmaceutical composition comprises a corticosteroid. In a further embodiment, the pharmaceutical composition does not contain one or more TZDs, but rather the one or more TZDs can be administered systemically. In certain embodiments the composition comprises both a corticosteroid and one or more TZDs, in this embodiment systemic exposure to the corticosteroid and one or more TZDs is reduced by using a topical, locally acting corticosteroid and one or more TZDs, instead of a systemically acting corticosteroid and one or more TZDs for the treatment of allergic or caustic gastrointestinal inflammation and/or fibrosis. In some embodiments, the topical, local delivery of the pharmaceutical composition does not provide substantial systemic exposure. In some embodiments, the inflamed and/or fibrotic portion of the gastrointestinal portion is at least partially coated, or substantially coated with the pharmaceutical composition. In certain embodiments, the effective amount of the pharmaceutical composition is an amount sufficient to coat the esophagus (e.g., a volume as set forth herein). In certain embodiments, the allergic or caustic inflammation and/or fibrosis of the gastrointestinal tract is the esophagus and the composition at least partially coats the esophagus (including all or part of the inflamed and/or fibrotic portion of the esophagus). In specific embodiments, the inflammation or fibrotic tissue of the gastrointestinal tract is associated with an allergic disease or disorder of the esophagus (e.g., eosinophilic esophagitis).

In certain embodiments, provided herein is a method of orally administering a composition comprising a corticosteroid and one or more TZDs wherein systemic exposure of corticosteroid and one or more TZDs is reduced (e.g., significantly reduced) compared to the pulmonary administration of a nebulized or aerosolized corticosteroid and TZD composition with the same nominal or delivered dose. In some embodiments, provided herein is a method of orally administering (e.g., by drinking or swallowing) a composition comprising a corticosteroid and one or more TZDs wherein systemic exposure of corticosteroid and one or more TZDs is reduced (e.g., significantly reduced) compared to the oral administration of a nebulized or aerosolized corticosteroid and TZD composition (which is sprayed on the targeted site of the gastrointestinal site, e.g., esophagus) comprising a corticosteroid and TZD.

It will be appreciated by those skilled in the art that reference herein to treatment extends to prophylaxis as well as the treatment of inflammation and fibrosis or other symptoms.

While the compositions of the disclosure will typically be used in therapy for human patients, they may also be used in veterinary medicine to treat similar or identical diseases. The compositions may, for example, be used to treat mammals, including, but not limited to, primates and domesticated mammals. The compositions may, for example, be used to treat herbivores. The compositions of the disclosure include geometric and optical isomers.

Pharmaceutical compositions suitable for use in the disclosure include compositions wherein the active ingredients are contained in an effective amount to achieve its intended purpose. Determination of the effective amounts is well within the capability of those skilled in the art, especially in light of the detailed disclosure provided herein.

Liquid suspensions of the disclosure include, for example, those prepared by adding about 5 to about 25 grams of sucralose (Splenda®, Distributed By: McNeil Nutritionals, LLC, Fort Washington, Pa. 19034-2299), or about 7 to about 20 grams of sucralose (Splenda®), or about 5 to about 15 grams of sucralose (Splenda®), or about or about 7 to about 15 grams of sucralose (Splenda®), or about 8 to about 12 grams of sucralose (Splenda®), or about 10 to about 11 grams of sucralose (Splenda®), or 1, 2, 3, 4, 5, 6, 7, 8, 9, 10, 11, 12, 13, 14, 15, 16, 17, 18, 19, 20, 21, 22, 23, 24, or 25 grams of sucralose (Splenda®), added to 2 mL or 4 mL of Budesonide and/or one or more TZDs. Smaller or larger volumes of formulations provided herein may also be used. In some embodiments, the volume used in a formulation provided herein comprises components in the ratios as described above.

The exact dosage will depend upon the route of administration, the form in which the composition is administered, the subject to be treated, the age, body weight/height of the subject to be treated, and the preference and experience of the attending physician. In certain embodiments, the optimal concentration of the corticosteroid and/or one or more TZDs in the composition depends upon the specific corticosteroid or TZD used, the characteristics of the patient, and the nature of the inflammation for which the treatment is sought. In various embodiments, these factors are determined by those of skill in the medical and pharmaceutical arts in view of the disclosure.

Generally, a therapeutically effective dose is desired. A therapeutically effective dose refers to the amount of the corticosteroid that results in a degree of amelioration of symptoms and/or inflammation relative to the status of such symptoms and/or inflammation prior to treatment; and the amount of the one or more TZDs that results in a degree of amelioration of symptoms and/or fibrosis relative to the status of such symptoms and/or fibrosis prior to treatment. The dosage forms and methods of applying dosage forms containing effective amounts are within the scope of the instant disclosure. In various embodiments, the amount of corticosteroid (e.g., budesonide) used in a method or in a composition described herein is from about 10 to 400 µg/kg of body weight per day, or for example, in the range of 20 to 300 µg/kg per day, or for example in the range of 30 to 200 µg/kg per day, or for example in the range of 30 to 100 µg/kg per day, or for example in the range of 35 to 100 µg/kg per day, or for example in the range of 40 to 100 µg/kg per day, or for example in the range of 35 to 60 µg/kg per day, or for example in the range of 10-50 µg/kg per day, or for example in the range of 10-100 µg/kg/day, or for example in the range of 30-50 µg/kg/day, or in an illustrative embodiment in the range of 40-60 µg/kg/day, about 2.5 to 400 µg/kg of body weight per day, or for example, in the range of 5 to 300 µg/kg per day, or for example in the range of 5 to 200 µg/kg per day, or for example in the range of 5 to 100 µg/kg per day, or for example in the range of 10 to 100 µg/kg per day, or for example in the range of 5-50 µg/kg/day, or in an illustrative embodiment in the range of 10-60 µg/kg/day or in an illustrative embodiment in the range of 30-60 µg/kg/day. In some embodiments, the amount of corticosteroid (e.g., budesonide) used in a method, in a composition or a dose of a composition disclosed herein includes, by way of non-limiting example, about 500 µg to about 2 mg, about 1 to about 2 mg, about 1 mg, about 2 mg, about 250 µg to about 20 mg, about 250 µg to about 15 mg, about 250 µg to about 10 mg, about 250 µg to about 5 mg, about 250 µg to about 3 mg, or about 500 µg to about 3 mg, about 375 µg to about 1.5 mg, or about 500 µg to about 2 mg, about 1 mg to about 3 mg, about 0.25 mg, about 0.35 mg, about 0.5 mg, about 1 mg, about 2 mg, about 2.5 mg, about 3 mg, about 4 mg, about 5 mg, about 6 mg, about 7 mg, about 8 mg, about 9 mg, about 10 mg, or any amount suitable. In an illustrative embodiment, the dosage is provided in a volume that reaches the esophagus in an effective amount.

In some embodiments, the amount of TZD (e.g., rosiglitazone) used in a method, in a composition or a dose of a composition disclosed herein includes, by way of non-limiting example, about 500 µg to about 8 mg, about 1 to about 2 mg, about 1 mg, about 2 mg, about 250 µg to about 7 mg, about 250 µg to about 6 mg, about 250 µg to about 5 mg, about 250 µg to about 4 mg, about 250 µg to about 3 mg, or about 500 µg to about 3 mg, about 375 µg to about 1.5 mg, or about 500 µg to about 2 mg, about 1 mg to about 3 mg, about 0.25 mg, about 0.35 mg, about 0.5 mg, about 1 mg, about 2 mg, about 2.5 mg, about 3 mg, about 4 mg, about 5 mg, about 6 mg, about 7 mg, about 8 mg, or any amount suitable between any of the foregoing per day. In an illustrative embodiment, the dosage is provided in a volume that reaches the esophagus in an effective amount.

In an illustrative embodiment, a dosage or amount (including a divided dose) of corticosteroid and one or more TZDs is provided in a volume that provides an effective amount of corticosteroid and one or more TZDs to reach the targeted inflamed and/or fibrotic portion of the gastrointestinal tract, including, e.g., the esophagus. In some embodiments, the effective volume of the composition coats or at least partially coats the esophagus, and delivers the composition to the affected areas, including by way of example only, the esophagus, a portion of the esophagus, the upper esophagus, the lower esophagus. In certain embodiments, a composition described herein has a volume of, for example about 5-50 mL, or for example about 5-40 mL, or for example about 5-30 mL, or for example about 5-25 mL, or for example about 5-15 mL, or for example about 10-25 mL, for example about 1-50 mL, or for example about 1-40 mL, or for example about 1-30 mL, or for example about 1-25 mL, or for example about 8-12 mL, or for example, about 7-8 mL, or for example, about 5-25 mL, or for example about 10-20 mL, or for example about 10 mL, or for example, about 15 mL, or for example, about 20 mL, or for example about 1-15 mL, or for example about 1-10 mL, or for example about 2-8 mL, or for example about 3-8 mL, or for example about 3-7 mL, or for example, about 4-6 mL, or for example, about 5 mL, or for example about 6-14 mL, or for example, about 4-15 mL, or for example, about 9-11 mL.

In more specific embodiments, about 0.25 mg to about 6 mg, about 0.375 mg, about 0.5 mg, about 0.75 mg, about 1 mg, about 1.25 mg, about 1.5 mg, or about 2 mg of corticosteroid (e.g., budesonide) and/or one or more TZDs is formulated into a single or unit dose of a pharmaceutical composition described herein, the single or unit dose having a total volume of about 10-20 mL, or for example about 10 mL, or for example, about 15 mL, or for example, about 20 mL, or for example about 1-15 mL, or for example about 1-10 mL, or for example about 2-8 mL, or for example about 3-7 mL, or for example about 4-6 mL, or for example, about 5 mL, or for example about 6-14 mL, or for example about 8-12 mL, or for example, about 9-11 mL, or for example, about 10 mL.

As discussed herein, "liquid" encompasses slurries, solutions, suspensions, or any combination thereof, depending on the solubilities and amounts of the individual components and the vehicles and solvents used. In some embodiments, provided herein is a composition comprising a corticosteroid and one or more TZDs in a formulation used to treat a targeted portion of the gastrointestinal tract (e.g., the esophagus). In further embodiments the composition comprises (or is administered in) a volume used to coat a targeted portion of the gastrointestinal tract (e.g., the esophagus). In certain embodiments the volume used to coat a targeted portion of the gastrointestinal tract (e.g., the esophagus) is a volume that is sufficient to coat the targeted portion. In some embodiments, an appropriate palatable dosage is in a volume that coats or at least partially coats the esophagus, and in an illustrative embodiment, the volume coats or at least partially coats the esophagus and delivers the corticosteroid and one or more TZDs to the affected areas, including by way of example only, the esophagus, a portion of the esophagus, the upper esophagus, or the lower esophagus. In certain instances, the volume of a composition administered can provide a desired coating characteristic of a composition. As such, in some embodiments, provided herein is a composition comprising a corticosteroid and one or more TZDs wherein the composition comprises (or is administered in) a volume sufficient to coat a targeted portion of the gastrointestinal tract (e.g., the esophagus). In certain embodiments, likewise, is provided herein a method of treating allergic or caustic inflammation and/or fibrosis of the gastrointestinal tract, or a symptom thereof, by administering to an individual in need thereof (e.g., one diagnosed with or suspected of suffering from eosinophilic esophagitis), a composition comprising a corticosteroid, one or more TZDs and a liquid vehicle, wherein the composition has a volume sufficient to coat (or at least coat in an effective amount) of a targeted portion of the gastrointestinal tract (e.g. esophagus). In specific embodiments, a volume sufficient to coat the esophagus is a volume that provides a bolus when orally administered to an individual. In more specific embodiments, a volume sufficient to coat the esophagus is a volume that provides a bolus along the entire length of the esophagus (i.e., from immediately after passing the upper esophageal sphincter through the distal end of the esophagus, e.g., immediately prior to entering or passing the lower esophageal sphincter. Thus, in certain embodiments described herein, a coating volume is optionally utilized instead of or in addition to a coating agent described herein in order to coat the targeted portion of the gastrointestinal tract (e.g., esophagus), as described herein.

In certain embodiments, provided herein are methods of treating, preventing or alleviating the symptoms of an allergic or caustic inflammation and fibrosis associated with inflammatory disorders involving the gastrointestinal tract, including the esophagus by administering a corticosteroid and one or more TZDs to an individual in need thereof. In some embodiments, the corticosteroid and one or more TZDs is administered along the length of (e.g., the entire length of) an afflicted or targeted surface of the gastrointestinal tract (e.g., the esophagus). In some embodiments, the corticosteroid and one or more TZDs are administered in a composition that coats the afflicted or targeted surface of the gastrointestinal tract (e.g., esophagus). In some embodiments, administration of corticosteroid and one or more TZDs or a composition described herein is achieved by nebulization or aerosolization of the corticosteroid and one or more TZDs or composition followed by swallowing (and, thereby, administration to the esophagus). In certain embodiments, administration of a corticosteroid and one or more TZDs or a composition described herein is administered with a nebulizer or inhaler. In some embodiments, the inhaler administers a composition of a corticosteroid and one or more TZDs, a vehicle (e.g., a solid, liquid or gaseous, such as a propellant, vehicle). Specific methods useful herein include administration from a multi-dose inhaler (MDI) or dry powder inhaler (DPI). In some embodiments, coating volumes include any suitable amount, e.g., about 2 mL or more, about 3 mL to about 20 mL, about 4 mL to about 15 mL, about 5 mL or more, about 5 mL to about 20 mL, about 5 mL to about 15 mL, or about 5 mL to about 10 mL. In some embodiments, the powder delivered from the device (such as a DPI or MDI) alone is the composition which coats or is delivered along the length of the afflicted or targeted gastrointestinal surface (e.g., esophagus).

The dosage may, for example, be administered at least once a day, e.g., in four, three, two, or one dose a day. In one illustrative example, the dose is provided once a day. In specific embodiments, administration of any composition described herein (e.g., for the treatment of gastrointestinal or esophageal inflammation and/or fibrosis including eosinophilic esophagitis) is once a day. In other specific embodiments, administration (e.g., for the treatment of gastrointestinal or esophageal inflammation and/or fibrosis including eosinophilic esophagitis) is b.i.d. In still other embodiments, administration (e.g., for the treatment of gastrointestinal or esophageal inflammation and/or fibrosis including eosinophilic esophagitis) is t.i.d. In yet other embodiments, administration (e.g., for the treatment of gastrointestinal or esophageal inflammation and/or fibrosis including eosinophilic esophagitis) is q.i.d. In another embodiment, the dose is administered at night. In another aspect, the dose is administered about 30 minutes prior to bed, with no food or water given after administration of the compositions herein. In yet another embodiment of the disclosure, the dose is administered prior to bedtime, wherein after administration of the composition, the patient or individual is in a substantially supine position for at least 30 minutes, at least 1 hour, at least 2 hours, at least 4 hours, at least 8 hours, about 30 minutes to about 8 hours, about 30 minutes to about 4 hours, about 1 hour to about 8 hours, or, about 1 hour to about 6 hours. In some embodiments provided herein, the dose is administered prior the individual being in a substantially supine position for at least 30 minutes, at least 1 hour, at least 2 hours, at least 4 hours, at least 8 hours, about 30 minutes to about 8 hours, about 30 minutes to about 4 hours, about 1 hour to about 8 hours, or, about 1 hour to about 6 hours. In specific embodiments, a corticosteroid and one or more TZDs or composition is administered according to any method described herein, wherein administration of the corticosteroid and one or more TZDs or composition is once a day, no more than once a day, more than once a day, twice a day, two to four times a day, three times a day, or four times a day. In some embodiments, the administration of the corticosteroid and one or more TZDs or composition provided herein is administered at night, e.g., not more than once a day at night.

In some embodiments, the corticosteroid and one or more TZDs is present in a pharmaceutical composition described herein in any effective amount. In some embodiments, an effective amount is an amount sufficient to reduce inflammation, inhibit fibrosis or treat fibrotic damage or symptoms associated with an allergic or caustic inflammatory disorder or condition of the gastrointestinal tract (e.g., the esophagus) as compared to the level of inflammation, fibrosis or symptoms of associated with an inflammatory disease prior to administration of the effective amount. In certain embodiments, effective amount is an amount sufficient to maintain a reduction in inflammation, fibrosis, fibrotic damage or symptoms of inflammation achieved in any manner including, but not limited to, by the administration of an effective amount sufficient to achieve such a reduction. In some embodiments, the effective amount is about 0.05 mg to about 10 mg, about 0.05 mg to about 7.5 mg, about 0.05 mg to about 5 mg, about 0.25 mg to about 3 mg, about 0.25 mg to about 2.5 mg, about 0.5 mg to about 3 mg, about 0.5 mg to about 2 mg, about 0.5 mg to about 0.1 mg, about 0.5 mg to about 5 mg, about 0.5 mg to about 4 mg, about 1 mg to about 4 mg, about 1 mg to about 3 mg, about 2 mg to about 3 mg, or about 2 mg to about 4 mg. In specific embodiments, the effective amount of corticosteroid is about 0.05 mg, about 0.1 mg., about 0.15 mg., about 0.25 mg., about 0.3 mg., about 0.35 mg, about 0.4 mg, about 0.37 mg, about 0.375 mg, about 0.7 mg, about 0.8 mg, about 0.75 mg, about 1 mg, about 1.2 mg, about 1.25 mg, about 1.3 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 6 mg or more, about 1 mg to about 6 mg, about 0.25 mg to about 6 mg, about 7.5 mg or more, about 0.5 mg to about 2 mg, about 1 to about 2 mg, about 1 mg, or about 2 mg of corticosteroid and one or more TZDs. In certain embodiments, the corticosteroid and one or more TZDs is present in a pharmaceutical composition at any concentration suitable for providing a therapeutically effective amount of corticosteroid and one or more TZDs to a surface of the gastrointestinal tract (e.g., the surface of the esophagus), e.g., a concentration of about 0.01 mg/mL to about 2 mg/mL of composition. In specific embodiments, the corticosteroid and one or more TZDs are each independently present in a pharmaceutical composition at a concentration of about 0.01 mg/mL to about 1.5 mg/mL, about 0.03 mg/mL to about 1.5 mg/mL, about 0.05 mg/mL to about 1.5 mg/mL, about 0.07 mg/mL to about 1.5 mg/mL, about 0.05 mg/mL to about 0.2 mg/mL, or about 0.06 mg/mL to about 0.13 mg/mL. In more specific embodiments, the corticosteroid and one or more TZDs is present in a pharmaceutical composition at a concentration of about 0.07 mg/mL to about 1 mg/mL. In some embodiments, any composition described herein comprises an amount or concentration of corticosteroid sufficient to provide about 0.5 mg to about 6 mg of corticosteroid per day and about 0.5 to about 8 mg per day of one or more TZDs, about 0.5 mg to about 2 mg of corticosteroid per day and about 0.5 to about 6 mg per day of one or more TZDs, about 1 mg to about 2 mg of corticosteroid per day and about 1 to about 5 mg per day of one or more TZDs, about 2 mg to about 3 mg of corticosteroid per day and about 2 to about 4 mg per day of one or more TZDs, about 3 mg to about 4 mg of corticosteroid per day and about 3 to about 5 mg per day of one or more TZDs, about 4 mg to about 5 mg of corticosteroid per day and about 2 to about 8 mg per day of one or more TZDs, or about 5 mg to about 6 mg of corticosteroid per day and about 3 to about 4 mg per day of one or more TZDs. In certain embodiments, provided herein is a method of treating allergic or caustic inflammation or fibrosis of the gastrointestinal tract, or a symptom thereof, by administering a sufficient amount of a composition described herein to provide about 0.5 mg to about 6 mg of corticosteroid per day and about 0.5 to about 8 mg per day of one or more TZDs, about 0.5 mg to about 2 mg of corticosteroid per day and about 0.5 to about 6 mg per day of one or more TZDs, about 1 mg to about 2 mg of corticosteroid per day and about 1 to about 5 mg per day of one or more TZDs, about 2 mg to about 3 mg of corticosteroid per day and about 2 to about 4 mg per day of one or more TZDs, about 3 mg to about 4 mg of corticosteroid per day and about 3 to about 5 mg per day of one or more TZDs, about 4 mg to about 5 mg of corticosteroid per day and about 2 to about 8 mg per day of one or more TZDs, or about 5 mg to about 6 mg of corticosteroid per day and about 3 to about 4 mg per day of one or more TZDs to an individual in need thereof.

In specific embodiments, the composition described herein is a composition comprising a corticosteroid, dextrose, maltodextrin, and a liquid vehicle. In another embodiment, the composition described herein is a composition comprising a corticosteroid, one or more TZDs, dextrose, maltodextrin, and a liquid vehicle.

In other illustrative embodiments of the disclosure, the Budesonide and one or more TZDs is provided in the form of a lozenge which may be dissolved in the mouth, thus reaching and coating the esophagus. The lozenge or other similar tablet, capsule, or other solid, would dissolve rapidly in the mouth or esophagus to produce a solution that can then coat the esophagus. Or, for children or other patients that may have difficulty with a dissolving lozenge, the lozenge may be ground or otherwise dissolved in a small volume of water or other pharmaceutically suitable liquid, for example, reaching a total volume presented in embodiments herein. In other illustrative embodiments of the disclosure, the Budesonide and one or more TZDs is provided in the form of a tablet, a capsule, or, for example a gel capsule, designed for slow release and delivery to the esophagus.

Initial treatment may continue, for example, for about 3 days to 2 weeks for an acute condition, or about 4 weeks to about 16 weeks for a chronic condition, or about 8 weeks to about 12 weeks for a chronic condition. Longer therapy may also be needed, such as, for example, therapy similar to chronic therapy for persistent asthma. Patients may, for example, be treated for up to 6 months, or up to one year. Maintenance treatment can last up to or longer than one year. Patients may be treated on a maintenance basis or on an as needed basis during a problematic episode, depending on the severity of the condition. Patients can also be treated on a rotating treatment basis, where treatment is provided for a period of time and then the patient is taken off of the drug for a period before treatment resumes again. When off the drug, the patient may be given no treatment, treatment with another medication, or treatment with a reduced dosage. Or, patients may be given treatment with a higher dose of the composition until a desired reduced disease state is achieved, and then continued on a lower dose of the composition.

The methods and compositions of the disclosure are used by individuals of any age. By "individual" is meant any animal, for example, a mammal, or, for example, a human, including, for example, patients in need of treatment. In some embodiments, the human is a child.

The compositions of the disclosure may include pharmaceutically acceptable salts. Pharmaceutically acceptable salts are generally well known to those of ordinary skill in the art and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

In one embodiment, provided herein is an oral pharmaceutical composition comprising a corticosteroid, one or more TZDs and a coating agent (e.g., a viscosity increasing agent, a mucoadhesive agent, a combination thereof, or an agent that both increases viscosity and mucoadhesion).

Depending on the specific conditions being treated, the compositions may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20th ed.) Lippincott, Williams & Wilkins (2000).

In other embodiments, the corticosteroid and the one or more TZDs are formulated into separate and distinct composition for administration using similar dosing and amounts as described above. In this way, an individual would take/administer one composition comprising the corticosteroid and a second composition In certain embodiments, the pharmaceutical compositions provided herein are used to treat, prevent or alleviate allergic or caustic inflammatory diseases and fibrosis involving the gastrointestinal tract, including the esophagus. In some embodiments, the pharmaceutical composition is in liquid form. Liquid forms include, by way of non-limiting example, emulsions, solutions, suspensions, syrups, slurries, dispersions, colloids and the like. Also provided are pharmaceutical compositions comprising a corticosteroid (e.g., a topical corticosteroid, such as, for example, budesonide) and one or more TZDs (e.g., rosiglitazone and/or pioglitazone) and a coating agent (e.g., a mucoadhesive agent) in the form of a dissolving tablet, a dissolving wafer, a capsule, or a gel capsule. In some embodiments, a pharmaceutical composition described herein is in liquid, semi-solid or solid (e.g., powder) form. In specific embodiments, a pharmaceutical composition described herein is in semi-solid form, e.g., a gel, a gel matrix, a cream, a paste, or the like. In some embodiments, semi-solid forms comprise a liquid vehicle. In some embodiments, semi-solid forms comprise a liquid vehicle. In some embodiments, the solid form is a solid dosage form, such a tablet, or a powder. In certain embodiments, solid dosage forms described herein comprise a solid vehicle (e.g., as used in a tablet), and/or a gaseous vehicle (e.g., as used in DPI).

In addition to the active or actives, various embodiments of the disclosure provide for pharmaceutical compositions that contain suitable pharmaceutically carriers comprising, e.g., acceptable excipients and/or auxiliaries. For example, in some embodiments, pharmaceutically acceptable carriers (e.g., excipients and/or auxiliaries) are used to formulate the corticosteroids and one or more TZDs or a TZD composition herein disclosed for the practice of the disclosure into dosages suitable for systemic administration is within the scope of the disclosure. Suitable pharmaceutically acceptable carriers (e.g., excipients and/or auxiliaries) well known in the art can be formulated into dosages suitable for oral administration. Such carriers (e.g., excipients and/or auxiliaries) enable the compositions of the disclosure to be formulated as tablets, pills, dragees, capsules, liquids, soft chews, creams, pastes, chewable tablets, gels or gel matrices, gums, syrups, slurries, suspensions, lozenges, and the like, for oral ingestion by a patient to be treated. In certain instances, oral formulations (e.g., suspensions, creams or gel matrices) are formulated such that upon oral administration, an interface layer between the oral formulation (e.g., suspension, cream or gel matrix) and a gastrointestinal surface (e.g., mucosal membrane or epithelium) is formed. In some instances, an oral formulation (e.g., suspensions, creams or gel matrices) in contact with a mucosal membrane delivers the active ingredient to the mucosal membrane via the interface layer and as the oral formulations (e.g., suspensions, creams or gel matrices) near the interface layer is depleted of the active ingredient, a concentration gradient results. In certain instances an osmotic delivery may occur. In some instances, portions of the oral formulations (e.g., suspensions, creams or gel matrices) with high concentrations of the active ingredient, relative to the portions of the oral formulations (e.g., suspensions, creams or gel matrices) proximate to the interface layer, replenishes the active ingredient (e.g., the corticosteroid and the TZD, or the TZD) in the portion of the oral formulations (e.g., suspensions, creams or gel matrices) proximate to the interface layer. In certain instances, upon oral administration of an oral formulation described herein to an individual, an interface layer is formed between a gastrointestinal surface (e.g., an esophageal mucosa/epithelium) and a mixture of the oral formulation (e.g., lozenge or dissolving or chewable tablet) and saliva of the individual.

Pharmaceutical preparations for oral use may be obtained by combining the corticosteroids and one or more TZDs with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, sucralose (Splenda®, Distributed By: McNeil Nutritionals, LLC, Fort Washington, Pa. 19034-2299), mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate. For dissolving tablets, appropriate excipients include those that increase the resulting liquid viscosity of the dissolved tablet, enabling it to reach the esophagus, for example, to coat the esophagus. Appropriate excipients may also, for example, include those that render the dissolving tablet palatable, such as sweeteners.

For liquid form, appropriate excipients may be added to increase the coating ability, liquid viscosity and/or the mucoadhesive character of the liquid composition. Appropriate excipients may also, for example, include those that render the liquid composition palatable. Excipients may include, for example, either sugars, including lactose, sucrose, sucralose (Splenda®, Distributed By: McNeil Nutritionals, LLC, Fort Washington, Pa. 19034-2299), maltodextrin, dextrose, mannitol, or sorbitol; honey; cellulose preparations, for example, maize starch, wheat starch, rice starch, potato starch, gelatin, gum tragacanth, methyl cellulose, hydroxypropylmethyl-cellulose, a carboxymethyl-cellulose (CMC) (e.g., sodium carboxymethyl-cellulose (NaCMC)), and/or polyvinylpyrrolidone (PVP: povidone).

Viscosity-enhancing excipients that are optionally utilized in certain embodiments of the pharmaceutical compositions described herein include, by way of non-limiting example, a crosslinked poly(acrylic acid) (e.g., Carbopol 974P), glycerine, a carbomer homopolymer, a carbomer copolymer, acacia (gum arabic), agar, aluminum magnesium silicate, sodium alginate, sodium stearate, bladderwrack, bentonite, carbomer, carrageenan, Carbopol, cellulose, ceratonia, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, polyethylene glycol (e.g. PEG 200-4500) gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose, carboxymethyl-cellulose (CMC) (including, e.g., sodium carboxymethyl-cellulose (NaCMC)), silicon dioxide, polyvinylpyrrolidone (PVP: povidone), Splenda® or combinations thereof.

Mucoadhesive agents to be used herein include, by way of non-limiting example, a soluble polyvinylpyrrolidone polymer (PVP), a carbopol, a crosslinked poly(acrylic acid) (e.g., Carbopol 974P), a carbomer homopolymer, a carbomer copolymer, a water-swellable, but water-insoluble, fibrous, cross-linked carboxy-functional polymer, a hydrophilic polysaccharide gum, one or more maltodextrin, alginate, a cross-linked aliginate gum gel, thiomers (e.g., thiolated chitosan, thiolated polycarbophil, thiolated alginate, thiolated cellulose derivatives, thiolated carboxymethyl cellulose, thiolated polyacrylic acid, or thiolated polyacrylates), PEGylated polymers (e.g., PEGylated polyacrylic acid or PEGylated polyacrylates), lectin, hydroxypropyl methyl cellulose (HPMC), cellulose derivatives, HPMA copolymers, a water-dispersible polycarboxylated vinyl polymer. In some embodiments, the mucoadhesive agent is a carbopol. In a specific embodiment, the mucadhesive agent is selected from, by way of non-limiting example, Carbopol 974P, Carbopol Ultrez 10, sodium alginate LF120 and sodium alginate H120L.

In some embodiments, mucoadhesive agents that may be used in certain embodiments of the compositions and methods described herein are described, for example, in U.S. Pat. Nos. 6,638,521, 6,562,363, 6,509,028, 6,348,502, 6,306, 789, 5,814,330, and 4,900,552, each of which is hereby incorporated by reference in its entirety.

In one non-limiting example, a mucoadhesive agent can be, by way of non-limiting example, at least one or at least two particulate components selected from titanium dioxide, silicon dioxide, and clay. In some embodiments, when the composition is not further diluted with any liquid prior to administration, the level of silicon dioxide is from about 3% to about 15%, by weight of the composition. In certain embodiments, silicon dioxide is selected from, by way of non-limiting example, fumed silicon dioxide, precipitated silicon dioxide, coacervated silicon dioxide, gel silicon dioxide, and mixtures thereof. In some embodiments, clay is selected from, by way of non-limiting example, kaolin minerals, serpentine minerals, smectites, illite or mixtures thereof. In certain embodiments, clay is selected from, by way of non-limiting example, laponite, bentonite, hectorite, saponite, montmorillonites or mixtures thereof.

In some embodiments, compositions described herein comprise maltodextrin. In some embodiments, compositions described herein comprise about 0.05 g of maltodextrin per mL of liquid vehicle to about 0.6 g of maltodextrin per mL of liquid vehicle. In certain embodiments, compositions described herein comprise about 0.1 g of maltodextrin per mL of liquid vehicle to about 0.6 g of maltodextrin per mL of liquid vehicle. In certain embodiments, compositions described herein comprise about 0.2 g of maltodextrin per mL of liquid vehicle to about 0.5 g of maltodextrin per mL of liquid vehicle. In some embodiments, compositions described herein comprise about 0.1 g of maltodextrin per mL of liquid vehicle to about 0.4 g of maltodextrin per mL of liquid vehicle. In certain embodiments, compositions described herein comprise about 0.2 g of maltodextrin per mL of liquid vehicle to about 0.4 g of maltodextrin per mL of liquid vehicle. In some embodiments, compositions described herein comprise about 0.2 g of maltodextrin per mL of liquid vehicle to about 0.3 g of maltodextrin per mL of liquid vehicle. In certain embodiments, compositions described herein comprise about 0.25 g of maltodextrin per mL of liquid vehicle to about 0.28 g of maltodextrin per mL of liquid vehicle. In some embodiments, compositions described herein comprise about 0.1 g of maltodextrin per mL of liquid vehicle, about 0.15 g of maltodextrin per mL of liquid vehicle, about 0.2 g of maltodextrin per mL of liquid vehicle, about 0.25 g of maltodextrin per mL of liquid vehicle, about 0.3 g of maltodextrin per mL of liquid vehicle, about 0.35 g of maltodextrin per mL of liquid vehicle, about 0.4 g of maltodextrin per mL of liquid vehicle, about 0.45 g of maltodextrin per mL of liquid vehicle, about 0.5 g of maltodextrin per mL of liquid vehicle, about 0.55 g of maltodextrin per mL of liquid vehicle, or about 0.6 g of maltodextrin per mL of liquid vehicle.

In some embodiments, a coating agent utilized herein comprises maltodextrin.

In some embodiments, a mucoadhesive agent utilized in an oral pharmaceutical composition described herein imparts an increased viscosity upon the oral pharmaceutical composition (e.g., compared to an otherwise identical composition lacking the mucoadhesive agent).

Any of the compositions or formulations described herein optionally comprise one or more viscosity enhancing agent, optionally comprise one or more binder, optionally comprise one or more filler, optionally comprise one or more lubricant, optionally comprise one or more solvent, optionally comprise one or more sweetener, optionally comprise one or more antioxidant, optionally comprise one or more buffering agent, optionally comprise one or more surfactant, or combinations thereof.

Buffering agents include, by way of non-limiting example, citrate buffers (i.e., citric acid and citrate), phosphate buffers, acetate buffers, combinations thereof, or the like.

Antioxidants include, by way of non-limiting example, ascorbyl palmitate, butylated hydroxyanisole, butylated hydroxytoluene, monothioglycerol, sodium ascorbate, sodium formaldehyde sulfoxylate, sodium metabisulfite, BHT, BHA, sodium bisulfite, vitamin E or a derivative thereof, propyl gallate, combinations thereof, or the like. Compositions and formulations described herein optionally include of about 0.01% w/w to about 0.5% w/w, about 0.01% w/w to about 0.3% w/w, or about 0.01% w/w to about 0.1% w/w one or more antioxidant(s).

In some embodiments, antioxidants include, by way of non-limiting example, edetate (EDTA) (e.g., disodium edetate), Diethylenetriaminepentaacetic acid (DTPA), Triglycollamate (NT), or the like. Compositions and formulations described herein optionally include about 0.01% w/w to about 0.5% w/w, about 0.01% w/w to about 0.3% w/w, or about 0.01% w/w to about 0.1% w/w, or about 0.05% w/w of edetate (or salt thereof).

In certain embodiments, sweeteners include, by way of non-limiting example, glycerin, sucrose, lactose, glucose, fructose, arabinose, xylose, ribose, mannose, galactose, dextrose, sorbose, sorbitol, mannitol, maltose, cellobiose, xylitol and the like.

Surfactants include, e.g., anionic, cationic, non-ionic, or zwitterionic surfactants, such as, by way of non-limiting example, polysorbate (e.g., polysorbate 20, polysorbate 60, polysorbate 40, polysorbate 80, polysorbate 81, polysorbate 85, polysorbate 120), bile acids or their salts (e.g., sodium taurocholates, sodium deoxytaurocholates, chenodeoxycholic acid, and ursodeoxycholic acid), nonoxynol or polyoxyethylene glycol fatty acid esters, pluronic or poloxamers such as Pluronic F68, Pluronic L44, Pluronic L101, combinations thereof, or the like. Compositions and formulations described herein optionally include about 0.001% w/w to about 0.5% w/w, about 0.001% w/w to about 0.3% w/w, or about 0.001% w/w to about 0.1% w/w of one or more surfactant.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active corticosteroid doses.

Pharmaceutical preparations that may be used orally also include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the corticosteroids may be dissolved or suspended in suitable liquids, such as fatty oils, liquid paraffin, or liquid polyethylene glycols (PEGs). In addition, stabilizers may be added.

In some embodiments, the corticosteroid and one or more TZDs are each administered independently in a commercially available formulation. In some embodiments, wherein the corticosteroid is budesonide, the commercially available formulation is Pulmicort Respules®. In certain embodiments, a composition provided herein comprises (1) commercially available micronized corticosteroid particles (e.g., micronized budesonide), or other commercially available corticosteroid particles; and (2) a diluent or vehicle (e.g., an aqueous liquid vehicle) to provide a composition as described herein (e.g., one having a volume sufficient to coat the esophagus). In some embodiments, a composition provided herein comprises (1) commercially available micronized corticosteroid particles (e.g., micronized budesonide), or other commercially available corticosteroid particles; (2) an excipient that increases the interaction of the composition and/or corticosteroid with a surface of the gastrointestinal tract (e.g., esophagus); and (3) optionally a diluent or vehicle (e.g., an aqueous liquid vehicle) to provide a composition as described herein (e.g., one having a volume sufficient to coat the esophagus). In specific embodiments, the commercially available micronized corticosteroid particles are provided in a suspension, e.g., a commercially available suspension such as Pulmicort Respules®. In certain embodiments, provided herein is a method of preparing such a composition by combining each of the components and mixing them together.

In certain embodiments, the corticosteroid containing composition comprises micronized budesonide, disodium edetate, sodium chloride, sodium citrate, citric acid, polysorbate (e.g., polysorbate 80), water, and optionally one or more excipients, wherein the excipients are selected from any of those recited herein. In a further embodiment, the composition further comprises one or more TZDs.

In one illustrative embodiment, the corticosteroid of the composition has a low bioavailability, so that much of it will remain in the gastrointestinal tract, for example, in the esophagus. This may result in decreased systemic side effects and complications, allowing patients with chronic conditions to receive treatment for longer periods of time. In certain embodiments, provided herein is a method of orally administering a composition comprising a corticosteroid wherein systemic exposure of corticosteroid is reduced (e.g., significantly reduced) compared to the pulmonary administration of a nebulized or aerosolized corticosteroid composition with the same nominal or delivered dose. In some embodiments, provided herein is a method of orally administering (e.g., by drinking) a composition comprising a corticosteroid wherein systemic exposure of corticosteroid is reduced (e.g., significantly reduced) compared to the oral administration of a nebulized or aerosolized corticosteroid composition (which is sprayed on the targeted site of the gastrointestinal site, e.g., esophagus) comprising a corticosteroid. In some embodiments, the area under the curve ($AUC_{0-\infty}$) for the plasma concentration of an orally administered corticosteroid composition described herein to the gastrointestinal tract according to any methods described herein is less than 90%, less than 80%, less than 70%, less than 60%, between 50% and 90%, between 0% and 40%, less than 50%, less than 40%, less than 30%, less than 20%, or less than 10% of the area under the curve ($AUC_{0-\infty}$) for the plasma concentration of an inhaled corticosteroid (e.g., Pulmicort) having the same delivered dose (or dose adjusted for the same dose as administered orally).

Excipients, such as, for example, those listed herein, may be included in the composition to increase the viscosity of the delivered composition. The liquid viscosity may be increased in the oral form, or the excipient may increase the viscosity of the dissolved form of a tablet. Those of ordinary skill in the art will recognize that the viscosity should be at a level that is sufficient to deliver an effective amount of the composition to the esophagus, for example, in an amount that may coat the esophagus. Also, the viscosity should be at a level that may be given orally, thus not so thick that it is either too difficult to swallow, causes gagging, or is unpalatable. Those of ordinary skill in the art may determine the viscosity of the compositions provided in the Examples, and may thus determine appropriate ranges. One method of determining whether the composition is sufficiently viscous is by determining whether the inflammation, or eosinophilic infiltration, of the esophagus is reduced after treatment with the corticosteroid.

Viscosity can be determined by any method that will measure the resistance to shear offered by the substance or preparation. Many viscometers are available to those in the pharmaceutical field, and include those built by, for example, Brookfield. Viscosity may be, for example, measured at room temperature, at about 20-25 degrees Celsius, or at about 37 degrees Celsius to mimic body temperature. The viscosity of a liquid generally decreases as the temperature is raised. In some embodiments of the disclosure, the viscosity is about the viscosity of about 1 grams, about 2 grams, about 3 grams, about 4 grams, about 5 grams, about 6 grams, about 7 grams, about 8 grams, about 9 grams, about 10 grams, about 11 grams, about 12 grams, about 13 grams, about 14 grams, about 15 grams, about 1 to about 5 grams, about 1 to about 50 grams, or about 5 to about 25 grams of sucralose (Splenda®, Distributed By: McNeil Nutritionals, LLC, Fort Washington, Pa. 19034-2299) added to 4 ml water, at 25 degrees Celsius. In an illustrative embodiment, the viscosity is about the viscosity of 10 grams of sucralose (Splenda®) added to 4 ml of water, at 25 degrees Celsius. In other embodiments, the viscosity is about the viscosity of 5 to 20 grams of sucralose (Splenda®) in 8 ml total liquid volume, at 25 degrees Celsius. In other embodiments, the viscosity is about the viscosity of 5 to 15 grams of sucralose (Splenda®) in an 8 ml total liquid volume, at room temperature. In other embodiments, the viscosity is about the viscosity of 8 to 12 grams of sucralose (Splenda®) in an 8 ml total liquid volume at 25 degrees Celsius. In some embodiments, the viscosity is between that of about a fruit nectar and commercial honey, where the viscosity is measured at 25 degrees Celsius.

In some embodiments, the viscosity of a composition provided herein is at least 2 centipoise (cP), at least 5 cP, at least 10 cP, at least about 25 cP, at least about 30 cP, at least about 35 cP, at least about 40 cP, at least about 50 cP, at least about 200 cP, at least about 225 cP, about 2 cP to about 10 cP, about 2 cP to about 25 cP, about 2 cP to about 50 cP, about 20 cP to about 50 cP, about 20 cP to about 100 cP, or about 50 cP to about 100 cP. In some embodiments, the viscosity of the composition is at least about 100 cP. In certain embodiments, the viscosity of the composition, measured at about 25 degrees Celsius, is about 50 cP to about 250,000 cP, about 50 cP to about 70,000 cP, about 50 cP to about 25,000 cP, about 50 cP to about 10,000 cP, about 50 cP to about 3,000 cP, or about 50 cP to about 2,000 cP. In one aspect, the viscosity of the composition, as measured at about 25 degrees Celsius, is from about 25 centipoise (cP) to about 800 cP, about 50 cP to about 800, or about 300 cP to about 800 cP (e.g., measured by a Brookfield viscometer). In another aspect, the viscosity of the composition may range from about 100 cP to about 200 cP, about 200 cP to about 300 cP, about 250 cP to about 600 cP or about 400 cP to about 600 cP. In specific embodiments, the viscosity of the formulation is about 30 cP, about 100 cP, about 200 cP, about 300 cP, about 400 cP, about 500 cP, or about 250,000 cP (e.g., as measured with a Brookfield viscometer at about 25 degrees Celsius equipped with an ultra low adapter).

EXAMPLES

Example 1

Reagents, human esophageal tissues, and primary human esophageal fibroblast isolation. Reagents, human esophageal tissues, and primary human esophageal fibroblast isolation TGF-β1 (5 ng/mL; R&D Systems, Minneapolis, MN), rosiglitazone (20 μM; Abcam, Boston, MA), pioglitazone (20 μM; Sigma-Aldrich, St. Louis, MO), budesonide (0.1 μM; St. Louis, MO), and IL-4 (10 ng/mL; R&D Systems, Minneapolis, MN) were used in cell culture experiments. Inactive EoE, defined as less than 15 eosinophils per high-power field (hpf), was achieved with EoE-directed therapy of topical fluticasone or budesonide, proton pump inhibitor, and/or elimination diet. Active EoE was defined as greater than or equal to 15 eosinophils per hpf. Human organ transplant donor esophagi served as normal controls and were provided by the National Disease Research Interchange and the Arkansas Regional Organ Recovery Agency Control. All histopathology slides, prepared from esophageal tissues from patients with EoE and normal non-EoE controls (Table 1), were reviewed separately by an internal pathologist who was blinded to therapy. All experiments were conducted with the approval from the institutional review board (IRB). Patients with EoE and their parents were assented/consented for data and biopsy collection per IRB protocol. Primary human esophageal fibroblasts (FBL) were isolated from patients with EoE and non-EoE controls (Table 2).

TABLE 1

Characteristics of archived slides of patients with EoE and normal non-EoE controls used for immunohistochemical staining:

| Identifier | Age | Sex | Race | Relevant therapy |
|---|---|---|---|---|
| Active EoE#1 | 2 | M | Hispanic | Not available |
| Active EoE#2 | 2 | M | Other | Non |
| Active EoE#3 | 3 | M | Caucasian | OVB |
| Active EoE#4 | 4 | M | Other | Not available |
| Active EoE#5 | 4 | M | Other | OVB, PPI |
| Active EoE#6 | 5 | M | Caucasian | Diet Restriction |
| Active EoE#7 | 6 | M | Caucasian | Not available |
| Active EoE#8 | 7 | M | Caucasian | OVB, PPI |
| Active EoE#9 | 14 | F | Caucasian | None |
| Active EoE#10 | 15 | F | Caucasian | None |
| Active EoE#11 | 16 | M | Caucasian | None |
| Inactive EOE#1 | 1 | M | Asian | None |
| Inactive EOE#2 | 2 | M | Caucasian | PPI |
| Inactive EOE#3 | 2 | M | Asian | Not available |
| Inactive EOE#4 | 8 | M | Other | Not available |
| Inactive EOE#5 | 11 | M | Caucasian | Not available |
| Non-EoE organ donor #1 | Not available | Not available | Not available | Not available |
| Non-EoE organ donor #2 | Not available | Not available | Not available | Not available |
| Non-EoE organ donor #3 | 11 | F | Black | Not available |
| Non-EoE organ donor #4 | 31 | Not available | Not available | Not available |
| Non-EoE organ donor #5 | 37 | M | Caucasian | Not available |

EoE, eosinophilic esophagitis;
F, female;
M, male;
OVB, oralviscous budesonide;
PPI, proton pump inhibitor

TABLE 2

Clinical characteristics of healthy donors and EoE patients.

| Identifier | Age | Sex | Race | Relevant Therapy |
|---|---|---|---|---|
| Healthy Donor #1 | 13 | F | Caucasian | None |
| Healthy Donor #2 | 20 | F | Caucasian | None |
| Healthy Donor #3 | 16 | M | Caucasian | None |
| Healthy Donor #4 | 28 | M | Caucasian | None |
| Healthy Donor #5 | 44 | F | Hispanic | None |
| Healthy Donor #6 | 34 | F | Caucasian | None |
| EoE #1 | 13 | F | Caucasian | PPI, Elimination diet, OVB |
| EoE #2 | 12 | M | Caucasian | PPI, Elimination diet |
| EoE #3 | 16 | M | Caucasian | OVB |
| EoE #4 | 5 | F | Other | Elimination diet |
| EoE #5 | 18 | M | Caucasian | Elemental Formula, Elimination Diet |
| EoE #6 | 14 | M | Caucasian | PPI, Flonase |
| EoE #7 | 12 | F | Other | Prednisone |
| EoE #8 | 11 | M | Caucasian | Elimination diet, OVB |
| EoE #9 | 4 | M | Caucasian | OVB |

F, female, M, male; PPI, proton-pump inhibitor; OVB, oral viscous budesonide.

TABLE 3

Human qPCR primer sequences. S, sense; AS, antisense

| | | |
|---|---|---|
| α-sma (SEQ ID NO: 1, 2) | 5'-CCGACCGAATGCAGAAGGA-3' | (S) |
| | 5'-ACAGAGTATTTGCGCTCCGAA-3' | (AS) |
| collagen-1α1 (SEQ ID NO: 3, 4) | 5'-CAGCCGCTTCACCTACAGC-3' | (S) |
| | 5'-TTTTGTATTCAATCACTGTCTTGCC-3' | (AS) |
| Ctgf (SEQ ID NO: 5, 6) | 5'-ACCAATGACAACGCCTC-3' | (S) |
| | 5'-AGATTTTGGGAGTACGGATG-3' | (AS) |
| gapdh (SEQ ID NO: 7, 8) | 5'-TGGTATCGTGGAAGGACTCAT-3' | (S) |
| | 5'-ATGCCAGTGAGCTTCCCGTTC-3' | (AS) |
| ppar-γ (SEQ ID NO: 9, 10) | 5'-TTAGATGACAGCGACTTGG-3' | (S) |
| | 5'-GTAGCAGGTTGTCTTGAATG-3' | (AS) |

Cell culture and stimulation. Human esophageal fibroblast cells were matched as closely as possible for sex, race, and passage. At sub-confluence, cells were serum starved overnight and treated with a TZD, budesonide, a combination, or vehicle for 2-3 hours followed by incubation with TGF-β1 or vehicle.

Preparation of total RNA and cDNA and quantitative PCR. Total RNA from fibroblast cultures was extracted using RNA STAT-60 (Tel-Test, Inc., Friendswood, TX) protocol, and oligo(dT)-primed cDNA was synthesized as previously described using the Qiagen RT-PCR kit and manufacturer's instructions. Quantitative real-time PCR (qPCR) primers are listed in Table 3; qPCR was carried out as previously described using the appropriate gene-specific primers, and relative gene expression was calculated using the method, with glyceraldehyde 3-phosphate dehydrogenase (gapdh) as the housekeeping gene (Rawson et al., J. Allergy Clin. Immunol., 138:791-800, 2016).

Western immunoblot analysis. Adherent cells were washed with ice-cold phosphate-buffered saline containing 1 mM sodium orthovanadate ($Na_3VO_4$) and lysed in ice-cold RIPA lysis buffer freshly prepared and supplemented with 1 mM $Na_3VO_4$, complete protease inhibitor cocktail, and 2 mM phenylmethylsulfonyl fluoride. Whole cell lysates were centrifuged at 14,000 g for 15 minutes at 4° C. Equivalent amounts of total proteins were loaded into each well and electrophoresed on NuPAGE 4-12% Bis-Tris gels (Life Technologies, Grand Island, NY), transferred to polyvinylidene difluoride membranes, blocked with 5% bovine serum albumin, incubated with primary antibodies overnight (1:1,000) at 4° C., detected using species-appropriate horseradish peroxidase-conjugated secondary antibodies, and quantified as previously described (Rawson et al., J. Allergy Clin. Immunol., 138:791-800, 2016).

Immunostaining and histologic assessment. Tissue sections (5 μm) were deparaffinized and hydrated before immunostaining, as previously described (41). After antigen retrieval, the slides were incubated with anti-PPAR-g (1:800; AbCam, Cambridge, MA) or isotype control. The samples were processed for immunohistochemistry using the appropriate species-specific secondary antibodies, as previously described (Rawson et al., J. Allergy Clin. Immunol., 138:791-800, 2016). All images were analyzed under identical light setting including magnification, gain, camera position, and background illumination.

Statistical analysis. Using GraphPad PRISM v8.2.0 (GraphPad Software, San Diego, CA), the analysis of variance and t-tests were performed to assess statistical significance, defined as P-values<0.05.

Figure 1E:
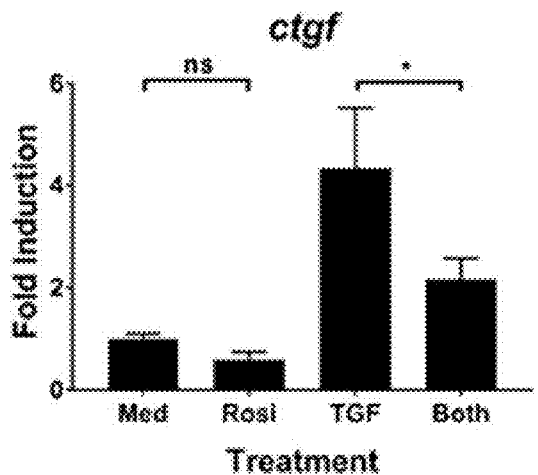
Figure 2B:
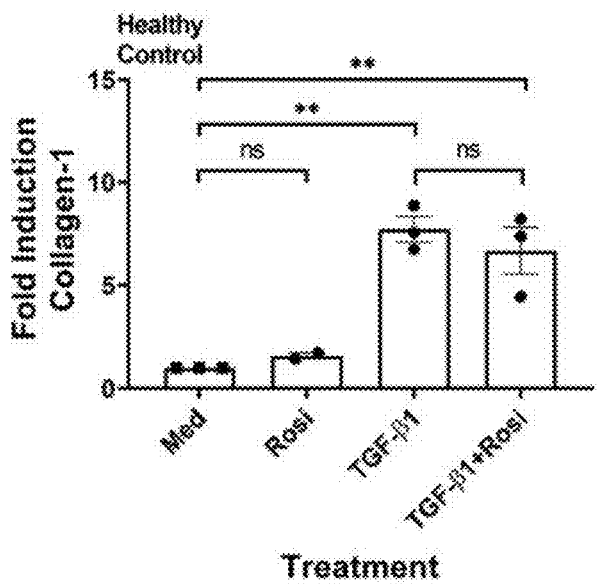
Figure 2C:
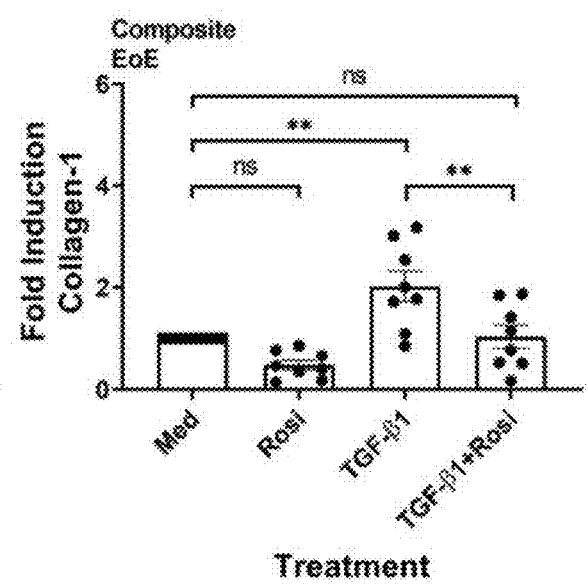
Figure 2D:
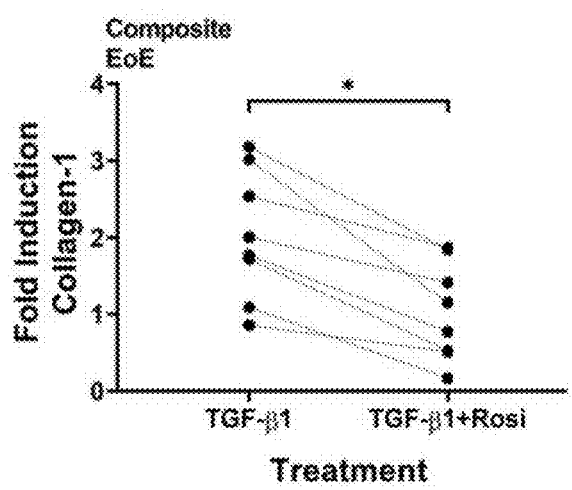
Figure 2E:
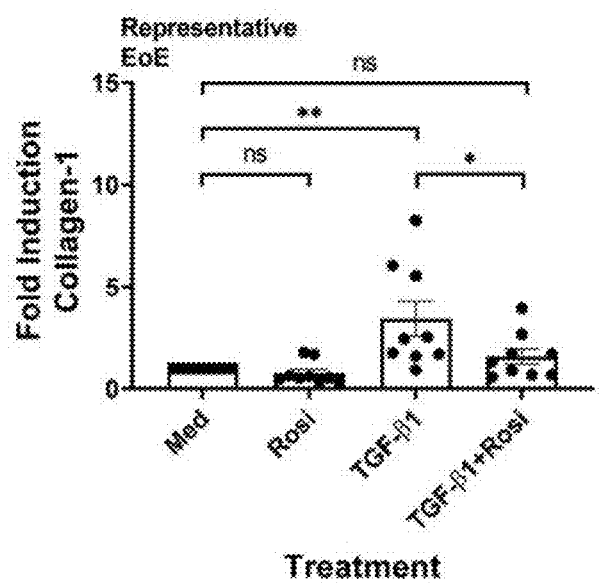
Figure 2F:
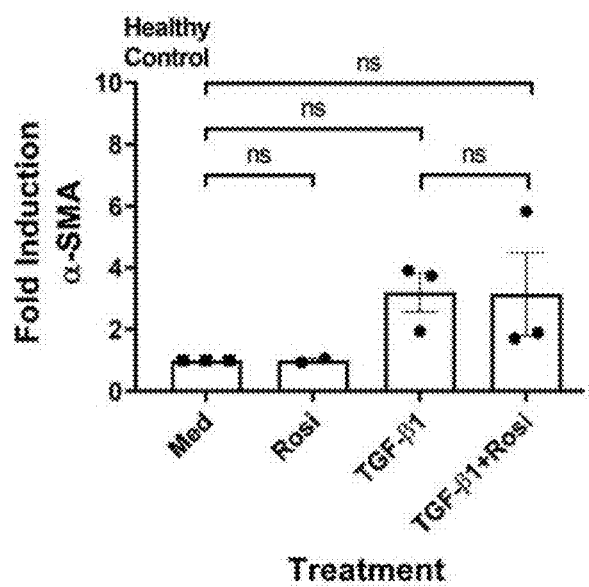
Figure 2G:
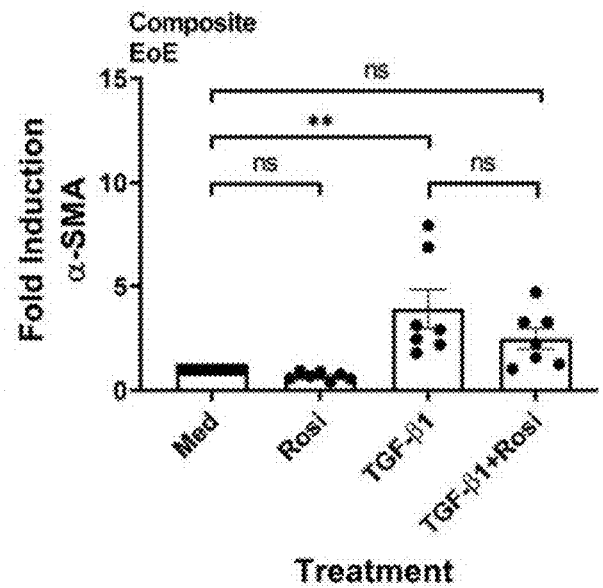
Figure 2H:
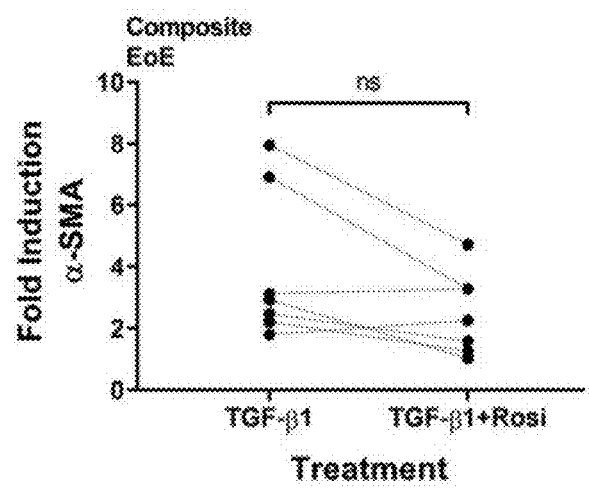
Figure 2I:
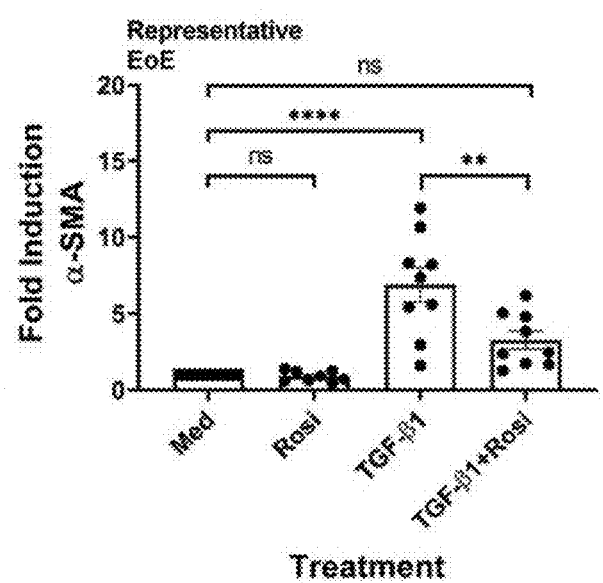

Rosiglitazone inhibits pro-fibrotic gene expression dose dependently in EoE-derived esophageal fibroblasts. Human primary esophageal fibroblasts were isolated from 6 healthy donors and 8 EoE patients (Table 2). To test the effects of TZDs on profibrotic gene expression in human esophageal fibroblasts, we treated cells with TGF-β1 in the absence or presence of rosiglitazone. TGF-β1 induced mRNA expression of α-smooth muscle actin (α-sma) in primary esophageal fibroblasts derived from healthy donors and patients with EoE (FIG. 1A). At the concentrations tested at up to 20 µM, as guided by the dose response studies in EoE cells, rosiglitazone exerted insignificant activities on basal and TGF-β1-induced α-sma gene expression in esophageal fibroblasts derived from healthy donors (FIG. 1A). By contrast, rosiglitazone significantly inhibited TGF-β1-induced mRNA expression of α-sma, collagen-1α1, and connective tissue growth factor (ctgf) in EoE esophageal fibroblasts (FIG. 1A-D). A dose-dependent effect of rosiglitazone was observed (FIG. 1E-F). A lack of reduction in the housekeeper gene expression and on responses in normal fibroblasts demonstrated that rosiglitazone effects were not due to toxicity at the concentrations used herein.

TZDs inhibit pro-fibrotic protein expression in EoE-derived esophageal fibroblasts. TGF-β1 induced protein expression of collagen-1α1 and α-sma in human primary esophageal fibroblasts (FIGS. 2 and 3). In esophageal fibroblasts isolated from patients with EoE, rosiglitazone reduced basal collagen-1 (FIG. 2A,C; n=8; P=0.0496) and inhibited TGF-β1-induced collagen-1 protein level (FIG. 2C-E; n=5 8; P=0.0192). By contrast, rosiglitazone did not inhibit basal protein expression of α-sma but did exhibit a trend toward reducing TGF-β1-driven α-sma protein in EoE-derived esophageal fibroblasts (FIG. 2A, G, F; N=7). This observation was validated by a significant reduction in biological replicates performed in a representative patient with EoE (FIG. 2I; P=0.0021). Consistent with its effects on mRNA expression, rosiglitazone did not inhibit TGF-β1-induced protein expression of α-sma and collagen-1α1 in normal esophageal fibroblasts (FIG. 2,A,B,F; N=3).

Figure 3A:
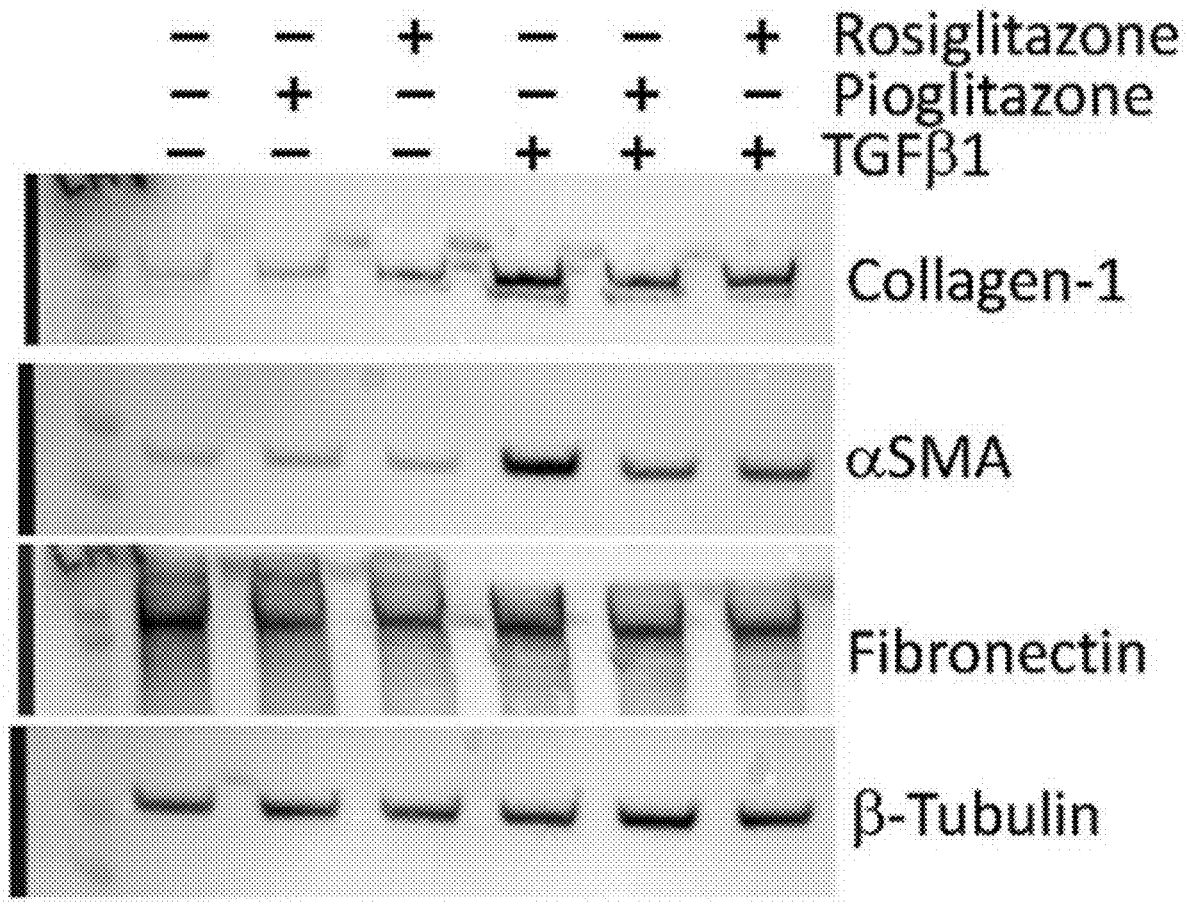
FIG. 3A-D shows EoE-derived primary esophageal fibroblasts respond to the TZDs. Human primary esophageal fibroblasts from a representative patient with EoE were stimulated with vehicle (dimethylsulfoxide), rosiglitazone (20 µM), or pioglitazone (20 µM) for 3 hours and then treated with TGF-β1 (5 ng/mL) for 24 hours in the presence or absence of vehicle, rosiglitazone, or pioglitazone (repeated in 3 separate experiments [A]). (B-D) Panels represent quantification of 3 separate experiments in cells derived from a representative patient with EoE. EoE, eosinophilic esophagitis; Med, medium; ns, not significant; pio, pioglitazone; rosi, rosiglitazone; TZD, thiazolidinediones. *$P<0.05$; $P<0.01$; *$P<0.001$; ****$P<0.0001$.
Figure 3B:
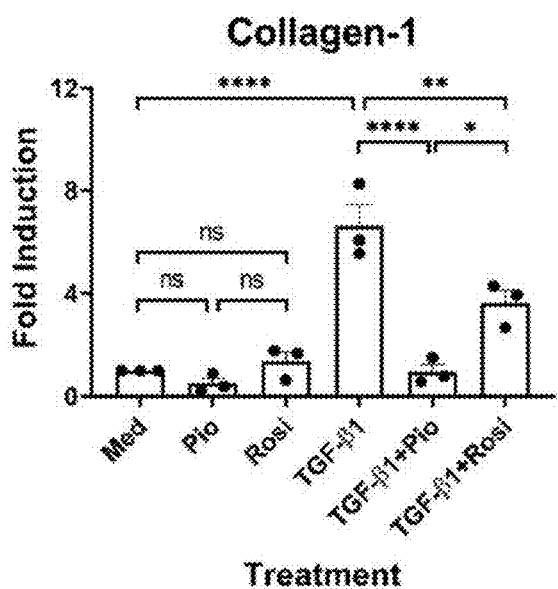
Figure 3C:
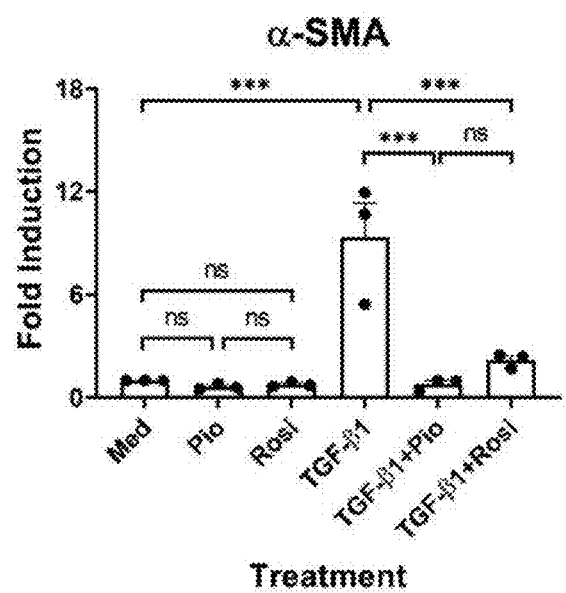
Figure 3D:
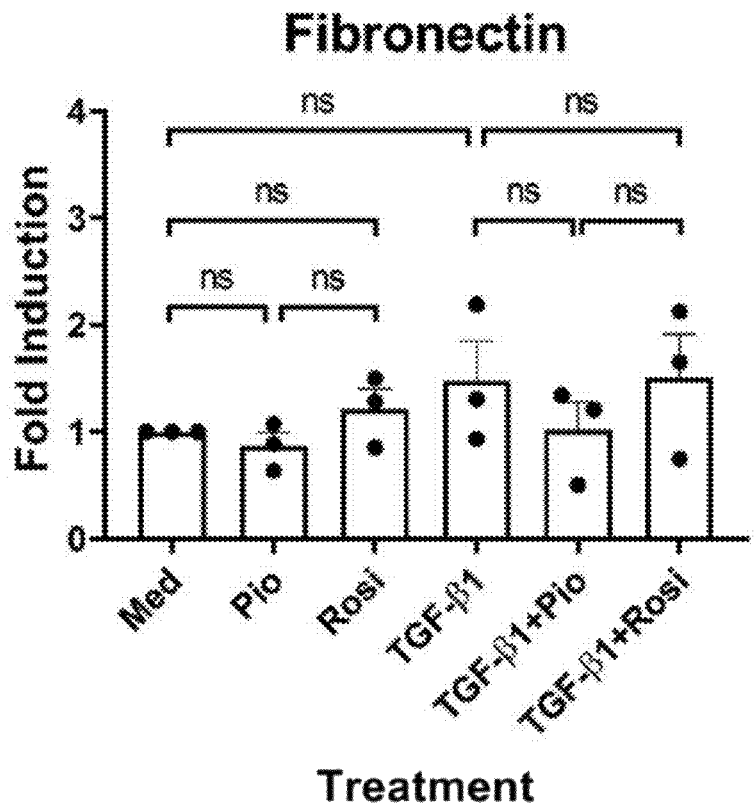

Next, the effects of pioglitazone, a TZD with a more favorable clinical profile than rosiglitazone, in esophageal fibroblasts isolated from a representative patient with EoE who responded to rosiglitazone. Pioglitazone also significantly decreased TGF-β1-mediated collagen-1α1 and α-sma induction in EoE-derived esophageal fibroblasts (FIG. 3A-C). However, the effects of rosiglitazone and pioglitazone on basal and TGF-β1-treated protein levels of fibronectin at the concentrations used herein were negligible (FIG. 3D). Taken together, these data suggested that EoE might induce a reprogramming of esophageal fibroblasts, with one of the downstream effects resulting in preferential increased responsiveness of EoE-derived cells to treatment with the TZDs, rosiglitazone and pioglitazone. Furthermore, the protein-specific effects of the TZDs suggested pathway-specific modulation of TGF-β1 signaling.

Figure 4A:
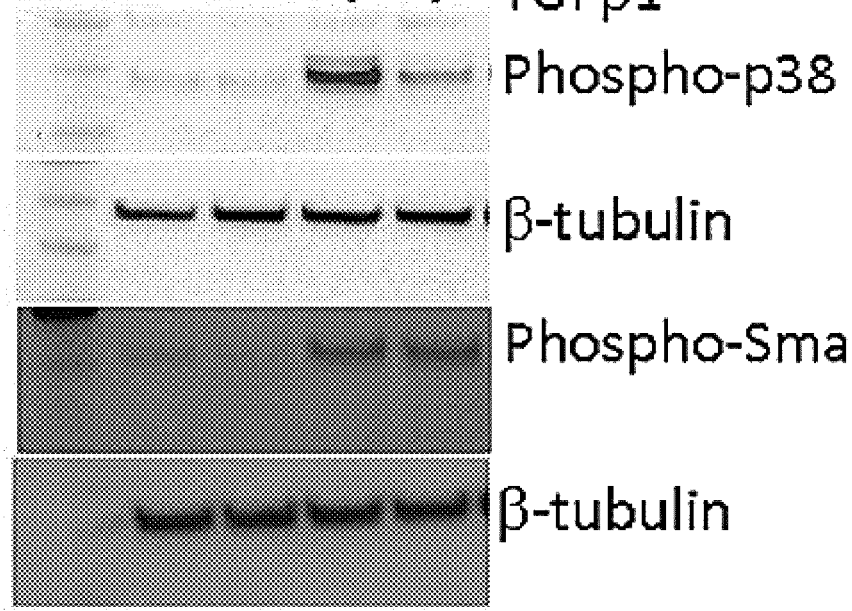
FIG. 4A-E shows Rosiglitazone inhibits p38 phosphorylation but has minimal effect on Smad2/3 phosphorylation in EoE-derived primary esophageal fibroblasts. Human primary esophageal fibroblasts from patients with EoE were treated with vehicle (dimethylsulfoxide) and rosiglitazone (20 µM) for 3 hours and then stimulated with TGF-β1 (5 ng/mL) for 30 minutes in the presence of vehicle or rosiglitazone. A representative blot is shown (A). (B and C) Panels represent quantification of blots of phospho-p38 and phospho-Smad2/3 in 4-5 different patients with EoE. A representative blot of a dose-response study using 2 or 20 µM rosiglitazone (D). (E) Panels represent quantification of blots of the dose-response study on phospho-p38 from 2 patients with EoE. EoE, eosinophilic esophagitis; Med, medium; R2, rosiglitazone (2 µM); R20, rosiglitazone (20 µM); TGF, TGF-β1. ns, not significant; *$P<0.05$; **$P<0.01$.
Figure 4B:
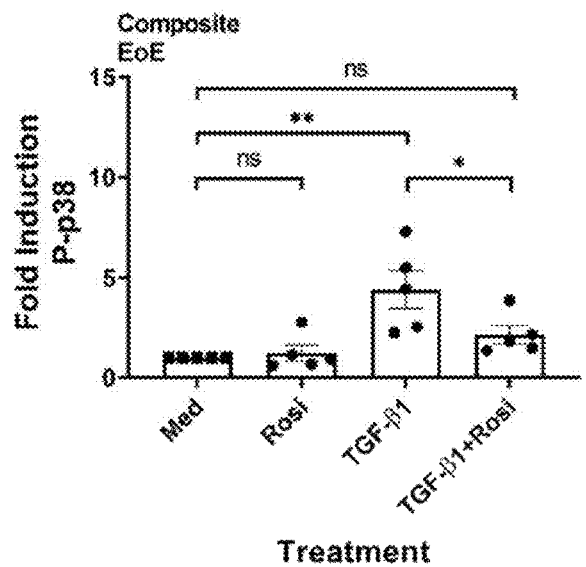
Figure 4C:
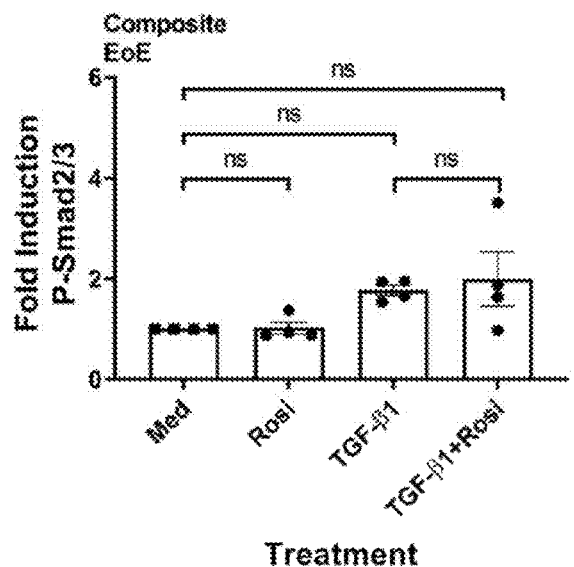
Figure 4D:
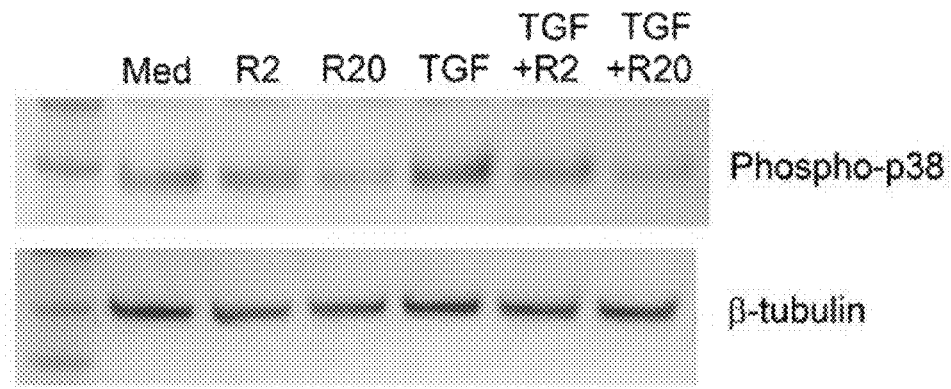
Figure 4E:
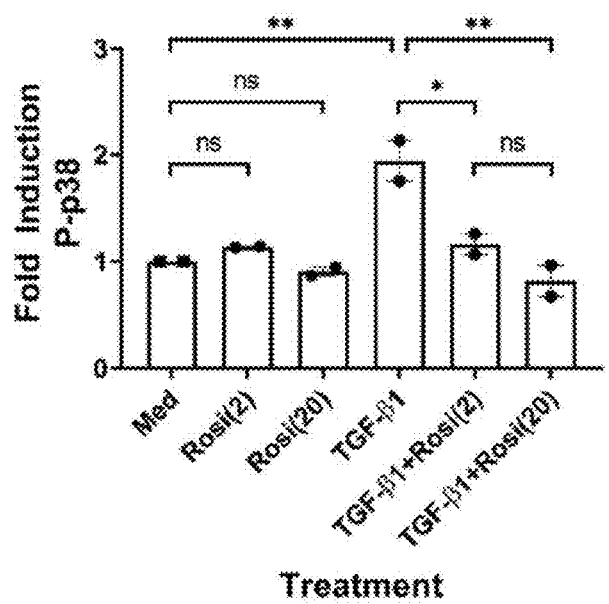

Rosiglitazone inhibits TGF-β1-induced phosphorylation of p38, but not Smad2/3, in EoE-derived esophageal fibroblasts. To better understand the distinct pathways affected by TZDs in esophageal fibroblasts, the effects of the drugs on p38 and pSmad2/3 were examined. As expected, TGF-β1 induced phosphorylation of both p38 and Smad2/3 in EoE-derived fibroblasts (FIG. 4A). Although rosiglitazone significantly inhibited p38 phosphorylation induced by TGF-β1, Smad2/3 phosphorylation was not affected (FIG. 4A-C). Rosiglitazone inhibited TGF-β1-induced p38 phosphorylation dose-dependently (FIG. 4D-E). Total p38 levels were unchanged basally, on stimulation with TGF-β1, or in the presence of rosiglitazone (data not shown). These results indicate that rosiglitazone may function, in part, via modulation of the noncanonical TGF-β1 signaling pathway leading to decreased p38 phosphorylation.

Figure 5A:
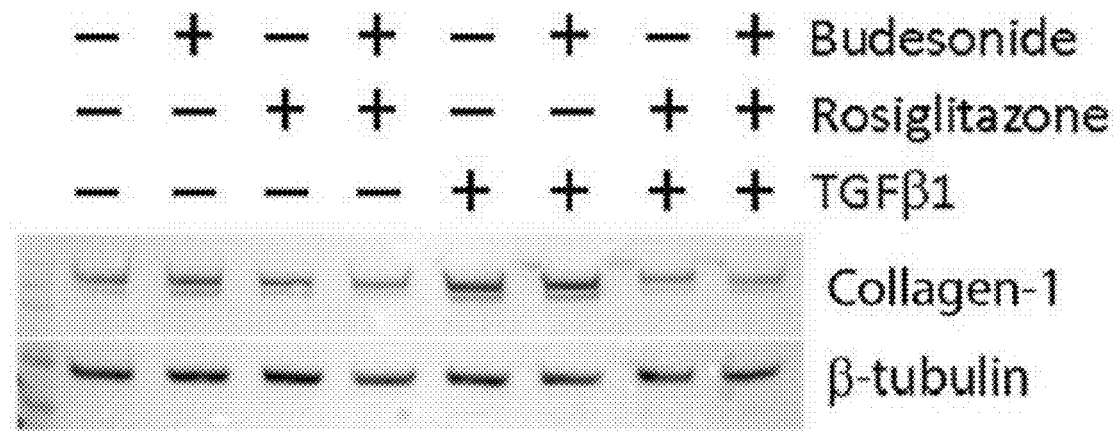
FIG. 5A-B shows a comparison of budesonide and rosiglitazone in EoE primary esophageal fibroblasts. EoE-derived esophageal fibroblasts from 2 patients were treated with vehicle, budesonide (0.1 µM), or rosiglitazone (20 µM) for 3 hours and then stimulated with TGF-β1 in the absence or presence of vehicle, budesonide, or rosiglitazone. Representative blot (A). (B) Quantification of blots from experiments from 2 separate patients with EoE. EoE, eosinophilic esophagitis; Med, medium; B, budesonide; R, rosiglitazone. ns, not significant; *$P<0.05$.
Figure 5B:
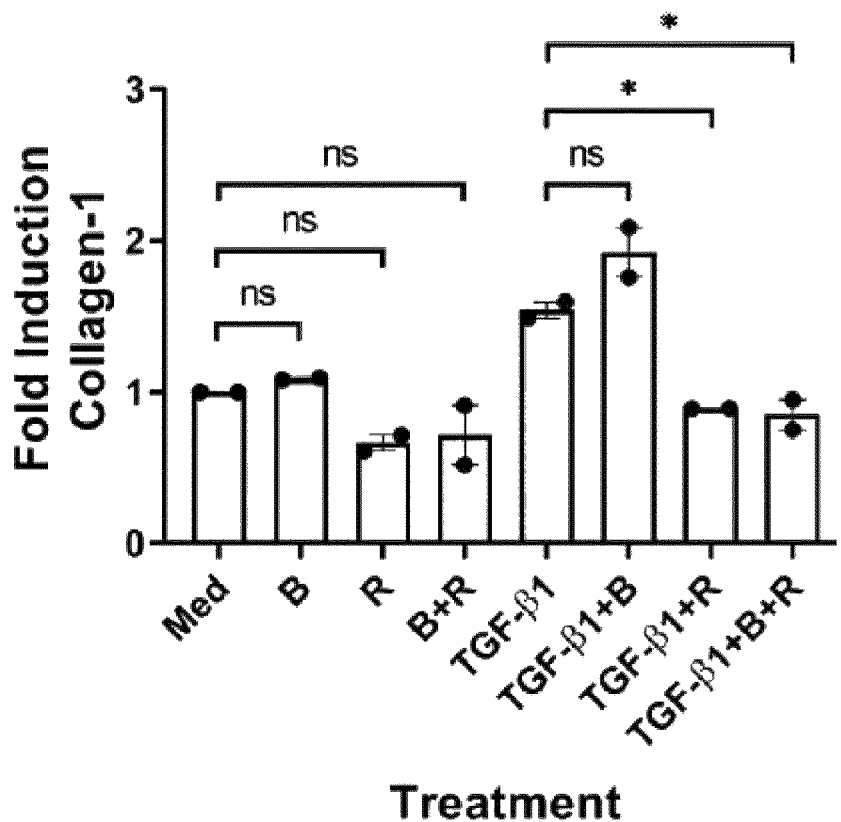

Comparison of rosiglitazone and budesonide in EoE fibroblasts. The effects of rosiglitazone with budesonide, a commonly used topical EoE therapy, were compared. In esophageal fibroblasts from 2 separate patients with EoE, budesonide had no effects on TGFβ1-induced protein expression of collagen-1α1 (FIG. 5). By contrast, rosiglitazone significantly reduced the expression of TGF-β1-induced collagen-1α1 protein level in EoE-derived fibroblasts. No synergistic effects were observed at the concentrations of budesonide and rosiglitazone used herein.

PPAR-γ is enriched in EoE-Derived Esophageal Biopsies and Fibroblasts.

Figure 6A:
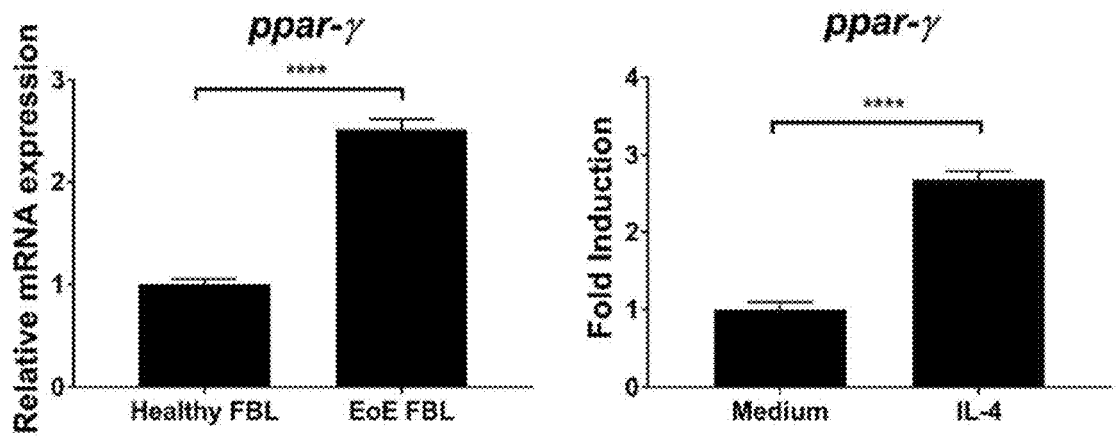
FIG. 6A-C shows PPAR-γ expression in human esophageal fibroblasts (FBL) and human esophageal biopsies. PPAR-γ mRNA expression was quantified in normal (N52) and EoE-derived esophageal fibroblasts (N52) basally (left) and after IL-4 (10 ng/mL) stimulation for 6 hours (right) (A). Representative images of EoE (fibrosis score 1, left panel; fibrosis score 3, middle panel) and normal control (right panel) biopsies stained for PPAR-γ protein expression (B). Insets show detail (400×, original magnification) and isotype control (2003). Quantification of PPAR-γ-positive staining in active EoE (N511), inactive EoE (N55), and normal controls (N55) (C). EoE, eosinophilic esophagitis; IL-4, interleukin-4; ns, not significant; PPAR-γ, peroxisome proliferator-activated receptor-γ. *$P<0.05$; $P<0.01$; **$P<0.0001$.

Given the observation that EoE esophageal fibroblasts had a preferential response to TZD-mediated down-regulation of TGF-β1 signals as compared to normal fibroblasts, the expression of PPAR-γ in normal and EoE esophageal biopsies and fibroblasts were compared. PPAR-γ mRNA expression was higher in EoE-derived fibroblasts as compared with normal (FIG. 6A). It was hypothesized that the Th2 cytokine, IL-4, might modulate the expression of PPAR-γ expression. Esophageal fibroblasts up-regulated PPAR-γ mRNA expression upon stimulation by IL-4 (FIG. 6A).

Figure 6B:
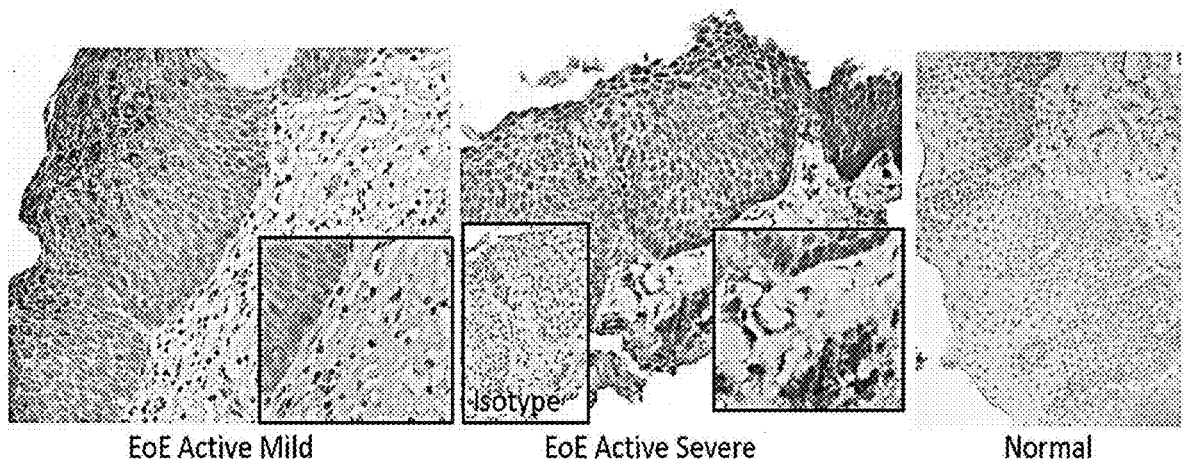
Figure 6C:
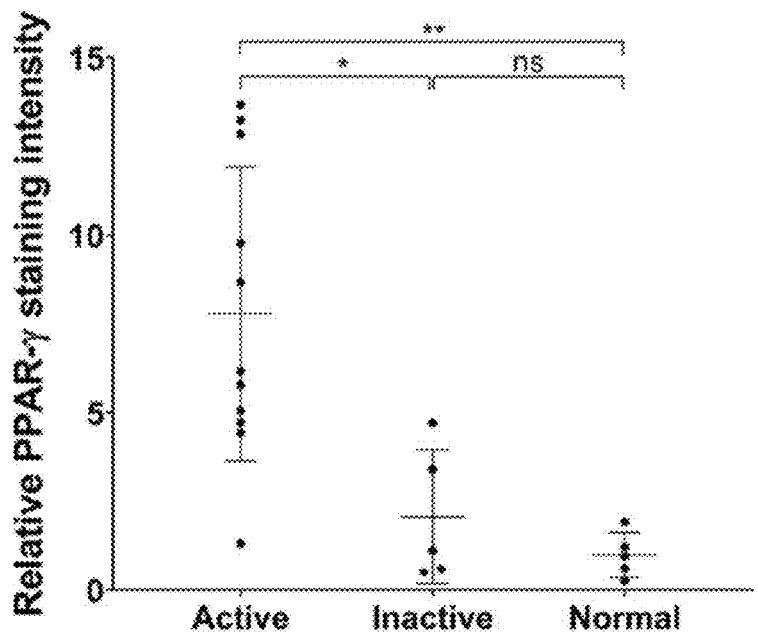

When assessing esophageal biopsies, it was found that active EoE esophageal biopsies, but not normal esophageal biopsies, had PPAR-γ expression in the epithelium and subepithelial lamina propria (FIG. 6B). Indeed, active EoE esophageal biopsies had higher expression of PPAR-g than inactive EoE esophagi and normal healthy esophagi (N=11 active EoE, 5 inactive EoE, and 5 normal biopsies, respectively) (FIG. 6C). Taken together, these results show that the Th2 inflammatory milieu in EoE upregulates PPAR-g expression, thereby rendering EoE cells more responsive to PPAR-g agonists.

At the concentrations used herein, up to 20 µM, as determined by dose-response studies in EoE cells, although normal esophageal fibroblasts were relatively resistant to the effects of the TZDs, fibroblasts derived from EoE biopsies were consistently sensitive to the TZDs at the mRNA and protein expression levels. The effect on p38 phosphorylation could be observed potently even at lower concentrations, e.g., 2 µM of rosiglitazone. The TZDs antagonized the noncanonical TGF-β1 pathway leading to diminished phosphorylated p38 levels while sparing the canonical TGF-β1-mediated Smad2/3 phosphorylation pathway. This observation for p38 phosphorylation is in congruence with previous reports that described the effects of the PPAR-γ ligands in fibroblasts from other human tissues. In addition, rosiglitazone had distinct effects on EoE esophageal fibroblasts as compared to budesonide. As such, the TZD class of drugs can function in vivo as adjuvant antifibrotic therapies in patients who have advanced, strictured, or steroid resistant EoE.

A number of embodiments of the invention have been described. Nevertheless, it will be understood that various modifications may be made without departing from the spirit and scope of the invention. Accordingly, other embodiments are within the scope of the following claims.

What is claimed is:

1. A method of preventing or alleviating esophageal inflammation and fibrosis in a subject comprising orally administering to the subject a pharmaceutical composition comprising a corticosteroid and one or more thiazolidinediones (TZD(s)) in an oral syrup formulation.

2. The method of claim 1, wherein the pharmaceutical composition is a suspension comprising corticosteroid microparticles.

3. The method of claim 1, wherein the pharmaceutical composition is administered once a day, twice a day, or three times a day.

4. The method of claim 1, wherein the pharmaceutical composition is administered once a day.

5. The method of claim 1, wherein the corticosteroid is a topical corticosteroid.

6. The method of claim 1, wherein the corticosteroid is budesonide.

7. The method of claim 1, wherein the one or more TZD(s) are selected from the group consisting of rosiglitazone, pioglitazone and a combination thereof.

8. The method of claim 1, wherein the oral syrup formulation comprises a viscosity enhancing excipient selected from the group consisting of lactose, sucrose, sucralose, maltodextrin, dextrose, mannitol, sorbitol, honey, maize starch, wheat starch, rice starch, potato starch, gelatin, gum tragacanth, methyl cellulose, hydroxypropylmethyl-cellulose, a carboxymethyl cellulose (CMC), sodium carboxymethyl-cellulose (NaCMC), polyvinylpyrrolidone (PVP: povidone), and combinations thereof.

9. The method of claim 1, wherein the esophageal inflammation is eosinophilic esophagitis.

10. The method of claim 1, wherein the subject has been diagnosed with a disease or condition selected from the group consisting of eosinophilic esophagitis, inflammatory bowel diseases involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, and post-surgery inflammation.

11. The method of claim 1, wherein the TZD is administered systemically and the corticosteroid is administered locally.

* * * * *